United States Patent
Kim et al.

(10) Patent No.: US 9,012,040 B2
(45) Date of Patent: *Apr. 21, 2015

(54) ANTHRACENE DERIVATIVE AND AN ORGANIC ELECTRONIC DEVICE USING THE SAME

(75) Inventors: Kong-Kyeom Kim, Daejeon (KR); Se-Hwan Son, Daejeon (KR); Dae-Woong Lee, Daejeon (KR); Sang-Young Jeon, Daejeon (KR); Hye-Young Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 565 days.

This patent is subject to a terminal disclaimer.

(21) Appl. No.: 13/003,530

(22) PCT Filed: Jul. 10, 2009

(86) PCT No.: PCT/KR2009/003799
§ 371 (c)(1),
(2), (4) Date: Jan. 10, 2011

(87) PCT Pub. No.: WO2010/005266
PCT Pub. Date: Jan. 14, 2010

(65) Prior Publication Data
US 2011/0114934 A1 May 19, 2011

(30) Foreign Application Priority Data
Jul. 11, 2008 (KR) .................. 10-2008-0067362

(51) Int. Cl.
*H01L 51/54* (2006.01)
*C07C 13/47* (2006.01)
(Continued)

(52) U.S. Cl.
CPC .............. *C07C 15/28* (2013.01); *C07C 211/61* (2013.01); *C07C 2103/24* (2013.01);
(Continued)

(58) Field of Classification Search
None
See application file for complete search history.

(56) References Cited

U.S. PATENT DOCUMENTS 5,638,308 A   6/1997   Stokes
6,465,115 B2  10/2002  Shi et al.
(Continued)

FOREIGN PATENT DOCUMENTS

KR  10-2007-0033383 A  3/2007
WO  WO 2005/091686 A1  9/2005
(Continued)

*Primary Examiner* — J. L. Yang
(74) *Attorney, Agent, or Firm* — McKenna Long & Aldridge LLP

(57) ABSTRACT

The present invention relates to a novel anthracene derivative and an organic electronic device using the same. An anthracene derivative that is represented by the following Formula 1:

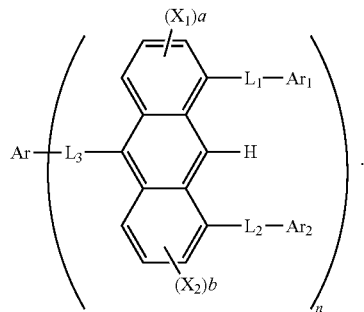

The anthracene derivative can act as a hole injecting, hole transporting, electron injecting and transporting, or light emitting material in an organic light emitting device and an organic electronic device. In particular, the anthracene derivative can act as a light emitting host. The organic electronic device according to the present invention has excellent characteristics in views of efficiency, the driving voltage, and the stability.

19 Claims, 1 Drawing Sheet

(51) Int. Cl.
| | |
|---|---|
| *C07C 49/788* | (2006.01) |
| *C07C 22/04* | (2006.01) |
| *C07D 235/06* | (2006.01) |
| *C07F 5/02* | (2006.01) |
| *C07D 213/06* | (2006.01) |
| *C07D 209/82* | (2006.01) |
| *C07C 15/28* | (2006.01) |
| *C07C 211/61* | (2006.01) |
| *C07D 209/86* | (2006.01) |
| *C07D 213/16* | (2006.01) |
| *C07D 213/38* | (2006.01) |
| *C07D 213/53* | (2006.01) |
| *C07D 215/06* | (2006.01) |
| *C07D 215/12* | (2006.01) |
| *C07D 221/12* | (2006.01) |
| *C07D 235/08* | (2006.01) |
| *C07D 239/26* | (2006.01) |
| *C07D 239/72* | (2006.01) |
| *C07D 333/08* | (2006.01) |
| *C07D 333/20* | (2006.01) |
| *C07D 401/14* | (2006.01) |
| *C07D 409/14* | (2006.01) |
| *H01L 51/00* | (2006.01) |

(52) U.S. Cl.
CPC ........... *C07D 209/86* (2013.01); *C07D 213/16* (2013.01); *C07D 213/38* (2013.01); *C07D 213/53* (2013.01); *C07D 215/06* (2013.01); *C07D 215/12* (2013.01); *C07D 221/12* (2013.01); *C07D 235/08* (2013.01); *C07D 239/26* (2013.01); *C07D 239/72* (2013.01); *C07D 333/08* (2013.01); *C07D 333/20* (2013.01); *C07D 401/14* (2013.01); *C07D 409/14* (2013.01); *H01L 51/0058* (2013.01); *Y02E 10/549* (2013.01)

(56) References Cited

U.S. PATENT DOCUMENTS

| | | |
|---|---|---|
| 2006/0154076 A1 | 7/2006 | Kubota et al. |
| 2006/0216633 A1 | 9/2006 | Kubota et al. |
| 2007/0088185 A1 | 4/2007 | Kubota et al. |
| 2007/0212568 A1 | 9/2007 | Wang |
| 2007/0285009 A1 | 12/2007 | Kubota et al. |
| 2008/0182129 A1* | 7/2008 | Klubek et al. ............... 428/704 |
| 2010/0025661 A1* | 2/2010 | Wang et al. .................. 257/40 |
| 2011/0108826 A1* | 5/2011 | Jang et al. .................... 257/40 |

FOREIGN PATENT DOCUMENTS

| | | | | |
|---|---|---|---|---|
| WO | WO 2006/003842 | * | 1/2006 | ............ C09K 11/06 |
| WO | WO 2006/003842 A1 | * | 1/2006 | ............ C09K 11/06 |

* cited by examiner

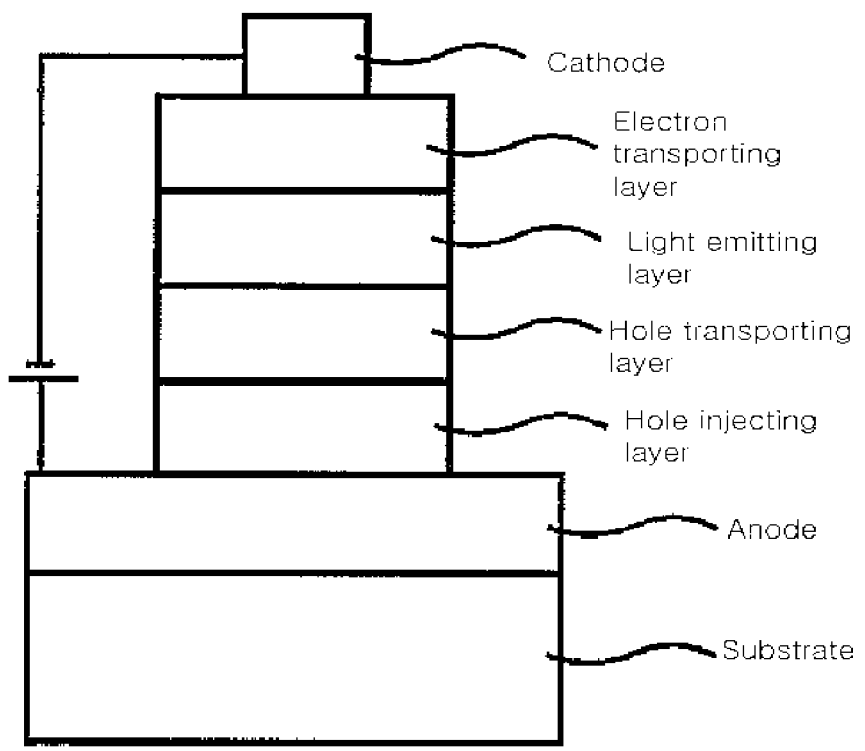

ANTHRACENE DERIVATIVE AND AN ORGANIC ELECTRONIC DEVICE USING THE SAME

TECHNICAL FIELD

The present invention relates to a novel anthracene derivative and an organic electronic device using the same. This application claims the benefit of PCT/KR2009/003799 filed on Jul. 10, 2009 and priority from Korean Patent Application No. 10-2008-0067362 filed on Jul. 11, 2008, both of which are incorporated herein by reference in their entirety.

BACKGROUND ART

The term, organic electronic device, refers to a device which requires electronic charge exchange between an electrode and an organic material by using holes and/or electrons. The organic electronic device can be largely classified into two types according to its operational principle as follows. One type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electric device having a configuration in which holes and/or electrons are injected into an organic material semiconductor forming an interface with an electrode by applying a voltage or current to two or more electrodes to allow the device to operate by means of the injected electron and hole.

Examples of the organic electronic device comprise an organic light emitting device, an organic solar cell, an organic photoconductor (OPC) and an organic transistor, which all require a hole injecting or transporting material, an electron injecting or transporting material, or a light emitting material for driving the device.

Hereinafter, the organic light emitting device will be mainly and specifically described, but in the above-mentioned organic electronic devices, the hole injecting or transporting material, the electron injecting or transporting material, or the light emitting material functions according to a similar principle.

In general, the term organic light emitting phenomenon refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into a light emitting material and a charge-transporting material, for example, a hole injecting material, a hole transporting material, an electron transporting material and an electron injecting material, according to their functions. The light emitting materials can be divided into a high molecule light emitting material and a low molecule light emitting material according to the molecular weight thereof, and can be divided into a fluorescent material that is derived from a singlet excite state of electrons and a phosphorescence material that is derived from a triplet excite state of electrons according to the light emitting mechanism. In addition, the light emitting materials can be divided into a blue, green or red light emitting material and a yellow or orange light emitting material required for giving more natural color, according to a light emitting color.

Meanwhile, in the case of when only one material is used as the light emitting material, the maximum light emitting wavelength is moved into the long wavelength by the interaction between molecules, the color purity is reduced, or efficiency of the device is lowered by the light emitting reducing effect. Accordingly, a host/dopant system can be used as the light emitting material for the purpose of enhancing the color purity and the light emitting efficiency through energy transfer. It is based on the principle that if a small amount of a dopant having a smaller energy band gap than a host which forms a light emitting layer is mixed with the light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired. The need to develop the above material is the same as the case of the above-mentioned other organic electronic devices.

In particular, the materials that comprise anthracene as the light emitting material are even well known as compared to pyrene or crycene derivatives (U.S. Pat. No. 5,638,308, U.S. Pat. No. 6,465,115, U.S. 2006-0154076, US 2006-0216633, US 2007-0285009, and US 2007-0088185). Among ten positions that can be substituted at the anthracene frame, the anthracene derivatives in which various substituent groups are introduced at 9,10-positions thereof, and trivalent and tetravalent anthracene materials in which additional substituent groups are introduced at positions other than 9,10-positions are disclosed. However, studies have hardly been made of characteristics such as a lifespan or efficiency of the light emitting material according to the substitution position change of anthracene. The above-mentioned anthracene derivatives are used as the blue and green light emitting materials, but there is a continuous need to improve a lifespan and efficiency of a device.

DISCLOSURE

Technical Problem

Therefore, the present inventors synthesized a novel anthracene derivative, and found that when these compounds are used in an organic material layer and a light emitting layer in an organic electronic device, efficiency of the organic electronic device is increased, the driving voltage is lowered, and the stability is increased, thereby accomplishing the present invention.

Accordingly, it is an object of the present invention to provide a novel anthracene derivative and an organic electronic device using the same.

Technical Solution

The present invention provides an anthracene derivative that is represented by the following Formula 1:

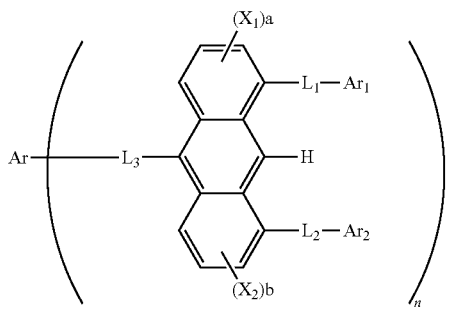

[Formula 1]

wherein n is an integer in the range of 1 to 3, in the case of when n is 2 or more, the structures in the parentheses are the same as or different from each other, $L_1$, $L_2$ and $L_3$ are the same as or different from each other, and are each independently a direct bond; or substituted or unsubstituted arylene, $Ar_1$ and $Ar_2$ are the same as or different from each other, and are each independently substituted or unsubstituted nonfused ring or fused ring aryl having 6 to 50 carbon atoms; substituted or unsubstituted nonfused ring or fused ring heteroaryl having 3 to 50 carbon atoms; substituted or unsubstituted fluorenyl; substituted or unsubstituted carbazolyl; or substituted or unsubstituted arylamine, Ar is substituted or unsubstituted nonfused ring or fused ring aryl having 6 to 50 carbon atoms; substituted or unsubstituted nonfused ring or fused ring heteroaryl having 3 to 50 carbon atoms; substituted or unsubstituted fluorenyl; substituted or unsubstituted carbazolyl; or substituted or unsubstituted arylamine, in the case of when n is 1 and $Ar_1$ and $Ar_2$ are substituted or unsubstituted aryl; substituted or unsubstituted heteroaryl; substituted or unsubstituted fluorenyl; or substituted or unsubstituted carbazolyl, Ar is carbazol that is subjected to N-substitution by hydrogen, substituted or unsubstituted alkyl having 1 to 24 carbon atoms, substituted or unsubstituted alkenyl having 2 to 24 carbon atoms, substituted or unsubstituted alkynyl having 2 to 24 carbon atoms, substituted or unsubstituted cycloalkyl having 3 to 20 carbon atoms, substituted or unsubstituted heterocycloalkyl having 3 to 20 carbon atoms, substituted or unsubstituted nonfused ring or fused ring aryl having 6 to 50 carbon atoms, substituted or unsubstituted nonfused ring or fused ring heteroaryl having 3 to 50 carbon atoms, substituted or unsubstituted fluorenyl, substituted or unsubstituted carbazolyl or substituted or unsubstituted arylamine; aryl that is substituted by substituted or unsubstituted nonfused ring or fused ring heteroaryl having 3 to 50 carbon atoms or substituted or unsubstituted carbazol; substituted or unsubstituted nonfused ring or fused ring heteroaryl that comprises N in the ring; phenylthienyl; or substituted or unsubstituted arylamine, a and b are an integer in the range of 0 to 3, in the case of when a is 2 or more, $X_1$s are the same as or different from each other, in the case of when b is 2 or more, $X_2$s are the same as or different from each other; and $X_1$ and $X_2$ are the same as or different from each other, and are each independently, hydrogen; substituted or unsubstituted alkyl having 1 to 24 carbon atoms; substituted or unsubstituted alkenyl having 2 to 24 carbon atoms; substituted or unsubstituted alkynyl having 2 to 24 carbon atoms; substituted or unsubstituted cycloalkyl having 3 to 20 carbon atoms; substituted or unsubstituted heterocycloalkyl group having 3 to 20 carbon atoms; substituted or unsubstituted nonfused ring or fused ring aryl having 6 to 50 carbon atoms; substituted or unsubstituted nonfused ring or fused ring heteroaryl having 3 to 50 carbon atoms; substituted or unsubstituted fluorenyl; substituted or unsubstituted carbazolyl; or substituted or unsubstituted arylamine.

In addition, the present invention provides an organic electronic device, which comprises a first electrode, a second electrode, and one or more organic material layers that are disposed between the first electrode and the second electrode. One or more of the organic material layers comprise an anthracene derivative.

Advantageous Effects

A novel anthracene derivative according to the present invention may act as a light emitting host in an organic electronic device. In addition, the anthracene derivative may act as a hole injecting, hole transporting, electron injecting and transporting, or light emitting material in an organic light emitting device and an organic electronic device. Accordingly, the organic electronic device according to the present invention has excellent characteristics in views of efficiency, the driving voltage, and the stability.

DESCRIPTION OF DRAWINGS

FIG. 1 is a view that illustrates a structure of an organic light emitting device according to an embodiment of the present invention.

BEST MODE

Hereinafter, the present invention will be described in detail.

An anthracene derivative according to the present invention is represented by Formula 1.

In the anthracene derivative that is represented by Formula 1 according to the present invention, the compounds that are represented by the following Formulas 2 to 5 are comprised.

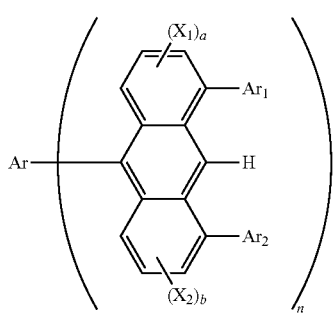

[Formula 2]

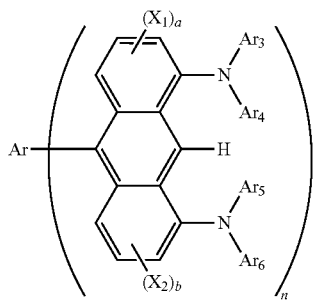

[Formula 3]

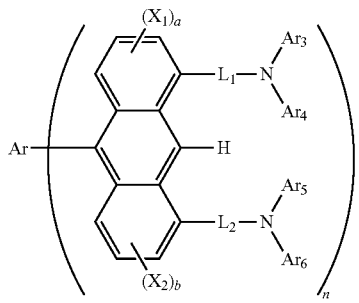

[Formula 4]

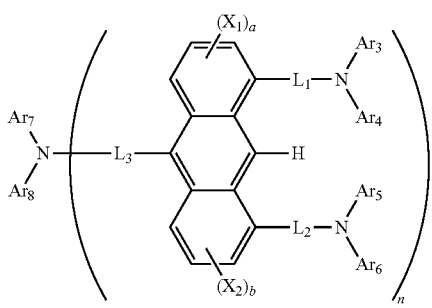

[Formula 5]

In Formulas 2 to 5, Ar, $X_1$, $X_2$, $Ar_1$, $Ar_2$, a, b and n are the same as those defined by Formula 1, and $Ar_3$ to $Ar_8$ are substituted or unsubstituted nonfused ring or fused ring aryl having 6 to 50 carbon atoms; or substituted or unsubstituted nonfused ring or fused ring heteroaryl having 3 to 50 carbon atoms.

Examples of the alkyl group comprise but are not limited to a methyl group, an ethyl group, a propyl group, an isopropyl group, a butyl group, a t-butyl group, a pentyl group, a hexyl group and a heptyl group.

Examples of the alkenyl group comprise but are not limited to a methenyl group, an ethenyl group, and a propylenyl group.

The cycloalkyl group is preferably a cycloalkyl group having 3 to 20 carbon atoms, which does not give steric hindrance. Preferable specific examples thereof comprise but are not limited to a cyclopentyl group and a cyclohexyl group.

Examples of the aryl group comprise a phenyl group, a naphthyl group, an anthracenyl group, a biphenyl group, penanthryl, pyrenyl, crycenyl, triphenylenyl, and perylenyl, but are not limited thereto. The aryl group comprises a group in which two or more aryl groups are bonded by a covalent bond.

As the heteroaryl group, there are pyrolyl, pyridyl, a bipyridyl group, indolyl, isoindolyl, furyl, benzofuranyl, isobenzofuranyl, quinolyl, isoquinolyl, quinoxalinyl, phenanthridinyl, acrydinyl, phenanthrolynyl, phenazynyl, phenothiadinyl, phenoxazynyl, furazynyl, thienyl, benzothienyl, isobenzothienyl, an imidazol group, and an oxazol group, but it is not limited thereto. The heteroaryl group comprises a group in which two or more heteroaryl groups are bonded by a covalent bond.

It is preferable that the arylamine group is an amine group that is substituted by a $C_6$~$C_{20}$ aryl group, and the aryl group may be substituted by the arylalkenyl group, but they are not limited thereto.

In the present invention, the term 'substituted or unsubstituted' means that substitution is carried out by at least one group that is selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_3$~$C_{20}$ heterocycloalkyl group, a $C_6$~$C_{50}$ aryl group and a $C_5$~$C_{50}$ heteroaryl group, and an arylamine group.

In the compound that is represented by Formula 1, in the case of when n is 1, it is preferable that at least one of Ar, $Ar_1$ and $Ar_2$ is substituted or unsubstituted arylamine.

In the compound that is represented by Formula 1, in the case of when n is 1 and $Ar_1$ and $Ar_2$ are substituted or unsubstituted aryl; substituted or unsubstituted heteroaryl; substituted or unsubstituted fluorenyl; or substituted or unsubstituted carbazolyl, it is preferable that Ar is carbazol that is subjected to N-substitution by hydrogen, substituted or unsubstituted alkyl having 1 to 24 carbon atoms, substituted or unsubstituted alkenyl having 2 to 24 carbon atoms, substituted or unsubstituted alkynyl having 2 to 24 carbon atoms, substituted or unsubstituted cycloalkyl having 3 to 20 carbon atoms, substituted or unsubstituted heterocycloalkyl having 3 to 20 carbon atoms, substituted or unsubstituted nonfused ring or fused ring aryl having 6 to 50 carbon atoms, substituted or unsubstituted nonfused ring or fused ring heteroaryl having 3 to 50 carbon atoms, substituted or unsubstituted fluorenyl, substituted or unsubstituted carbazolyl or substituted or unsubstituted arylamine; aryl that is substituted by nonfused ring or fused ring heteroaryl having 3 to 50 carbon atoms or carbazol; substituted or unsubstituted nonfused ring or fused ring heteroaryl that comprises N in the ring; phenylthienyl; or substituted or unsubstituted arylamine.

In the compound that is represented by Formula 1, in the case of when n is 2, it is preferable that Ar is a group selected from the group consisting of the following structural formulas.

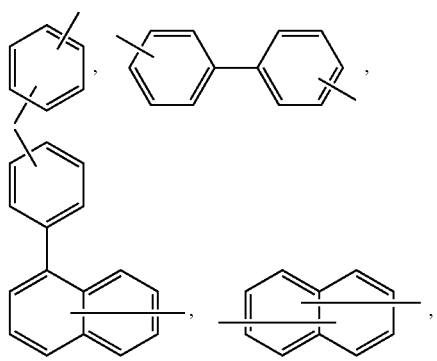

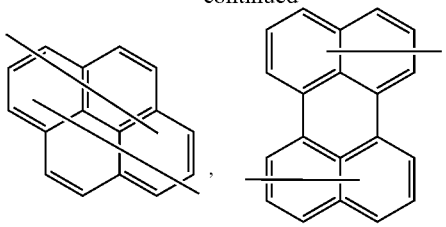

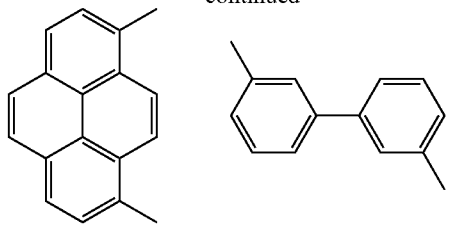

The above group may be substituted by one or more groups that are selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_3$~$C_{20}$ heterocycloalkyl group, a $C_6$~$C_{50}$ aryl group, a $C_5$~$C_{50}$ heteroaryl group, and an arylamine group.

In the compound that is represented by Formula 1, it is more preferable that Ar is selected from the groups that are represented by the following structural formulas, and these groups may be substituted by one or more groups that are selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_3$~$C_{20}$ heterocycloalkyl group, a $C_6$~$C_{20}$ aryl group, a $C_5$~$C_{20}$ heteroaryl group, and an arylamine group.

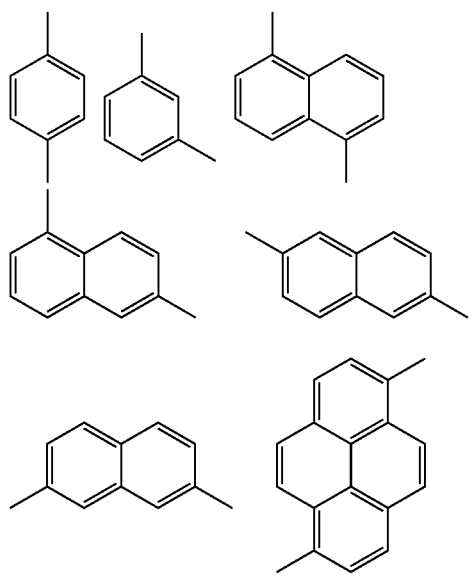

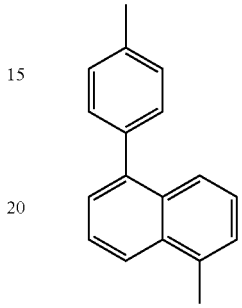

In the compound that is represented by Formula 1, it is preferable that $Ar_1$ and $Ar_2$ are a phenyl group, a biphenyl group, a naphthalene group, an anthracenyl group, or a substituted or unsubstituted $C_6$~$C_{50}$ aryl group.

According to an embodiment of the present invention, $Ar_1$ and $Ar_2$ of Formula 1 are each independently a phenyl group, a pyridyl group, a naphthyl group, a biphenyl group or an arylamine group.

According to an embodiment of the present invention, Ar of Formula 1 is a phenyl group, a naphthyl group, a pyridyl group, a quinolynyl group, a carbazolyl group, a thiophene group, a quinazolynyl group, an acrydyl group, a fluorenyl group, a pyrenyl group, an anthracenyl group or an arylamine group.

According to an embodiment of the present invention, $L_1$, $L_2$ and $L_3$ of Formula 1 are each independently a direct bond or a perylene group.

According to an embodiment of the present invention, $X_1$ and $X_2$ of Formula 1 are hydrogen.

In the compound that is represented by Formula 1, the compounds in which n is 1 are described in the following Table 1, but the scope of the present invention is not limited to the compounds described in the following Table 1.

TABLE 1

| Formula | Ar | $Ar_1$ | $Ar_2$ | $L_1$ | $L_2$ | $L_3$ | $X_1$ | $X_2$ |
|---|---|---|---|---|---|---|---|---|
| 1-1 | pyridyl | phenyl | phenyl | direct bond | direct bond | phenylene | H | H |
| 1-2 | quinolinyl | phenyl | phenyl | direct bond | direct bond | phenylene | H | H |

TABLE 1-continued
| Formula | Ar | Ar₁ | Ar₂ | L₁ | L₂ | L₃ | X₁ | X₂ |
|---|---|---|---|---|---|---|---|---|
| 1-3 | 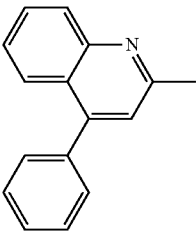 | 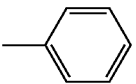 | 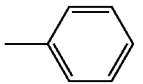 | direct bond | direct bond | 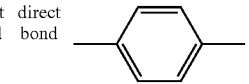 | H | H |
| 1-4 | 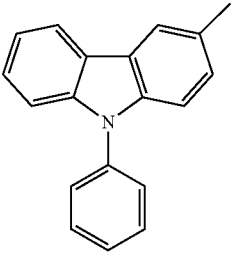 | 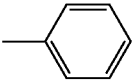 | 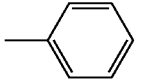 | direct bond | direct bond | 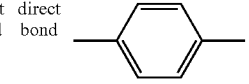 | H | H |
| 1-5 | 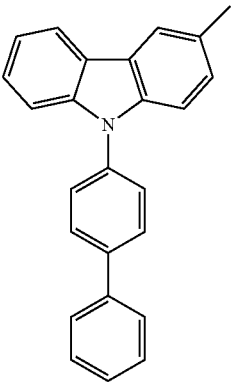 | 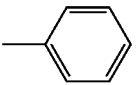 | 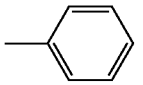 | direct bond | direct bond | 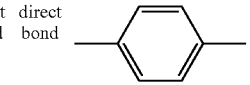 | H | H |
| 1-6 | 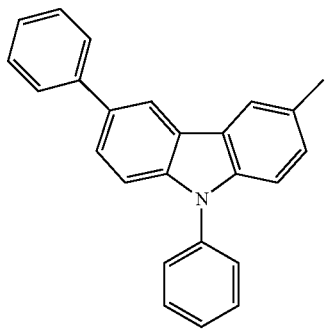 | 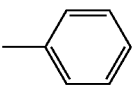 | 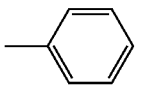 | direct bond | direct bond | direct bond | H | H |
| 1-7 | 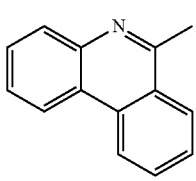 | 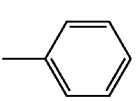 | 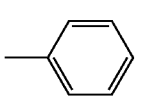 | direct bond | direct bond | 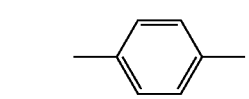 | H | H |

TABLE 1-continued

| Formula | Ar | Ar₁ | Ar₂ | L₁ | L₂ | L₃ | X₁ | X₂ |
|---------|----|----|----|----|----|----|----|----|
| 1-8 | 9-phenyl-3-methylcarbazole | phenyl | phenyl | direct bond | direct bond | direct bond | H | H |
| 1-9 | 5-phenyl-2-(4-methylphenyl)thiophene | phenyl | phenyl | direct bond | direct bond | 1,4-phenylene | H | H |
| 1-10 | 5-phenyl-2-methylthiophene | phenyl | phenyl | direct bond | direct bond | 1,3-phenylene | H | H |
| 1-11 | 5-phenyl-2-methylthiophene | 2-pyridyl | 2-pyridyl | direct bond | direct bond | 1,4-phenylene | H | H |
| 1-12 | 2-methylpyridine | 2-pyridyl | 2-pyridyl | direct bond | direct bond | 1,4-phenylene | H | H |
| 1-13 | 2-methylquinoline | 2-pyridyl | 2-pyridyl | direct bond | direct bond | 1,4-phenylene | H | H |
| 1-14 | 4-phenyl-2-methylquinoline | 2-pyridyl | 2-pyridyl | direct bond | direct bond | 1,4-phenylene | H | H |

TABLE 1-continued

| Formula | Ar | Ar₁ | Ar₂ | L₁ | L₂ | L₃ | X₁ | X₂ |
|---|---|---|---|---|---|---|---|---|
| 1-15 | N-phenylcarbazole with methyl | 2-pyridyl | 2-pyridyl | direct bond | direct bond | direct bond | H | H |
| 1-16 | N-(biphenyl)carbazole with methyl | 2-pyridyl | 2-pyridyl | direct bond | direct bond | phenylene | H | H |
| 1-17 | 3-phenyl-N-phenylcarbazole with methyl | 2-pyridyl | 2-pyridyl | direct bond | direct bond | phenylene | H | H |
| 1-18 | phenanthridine with methyl | 2-pyridyl | 2-pyridyl | direct bond | direct bond | phenylene | H | H |
| 1-19 | 4-phenylquinazoline with methyl | 2-pyridyl | 2-pyridyl | direct bond | direct bond | phenylene | H | H |

TABLE 1-continued
| Formula | Ar | Ar₁ | Ar₂ | L₁ | L₂ | L₃ | X₁ | X₂ |
|---|---|---|---|---|---|---|---|---|
| 1-20 | 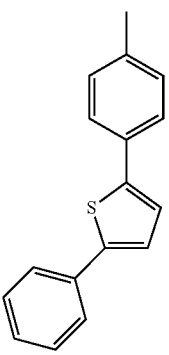 | 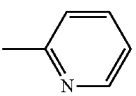 | 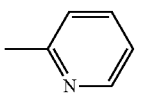 | direct bond | direct bond | 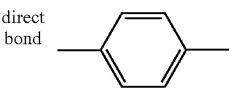 | H | H |
| 1-21 | 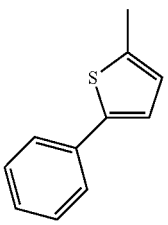 | 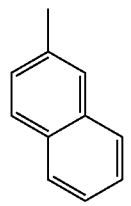 | 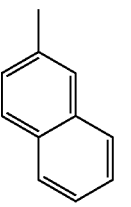 | direct bond | direct bond | 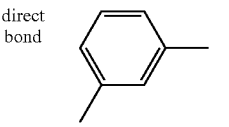 | H | H |
| 1-22 | 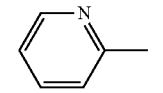 | 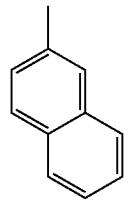 | 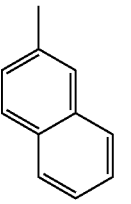 | direct bond | direct bond | 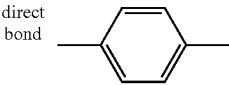 | H | H |
| 1-23 | 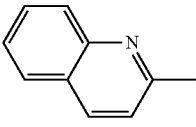 | 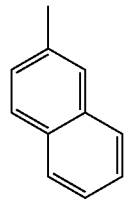 | 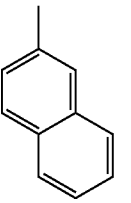 | direct bond | direct bond | 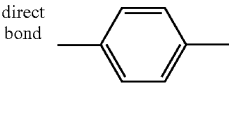 | H | H |
| 1-24 | 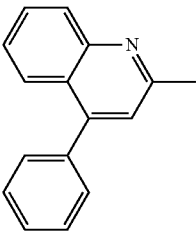 | 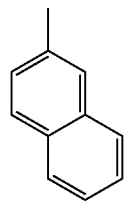 | 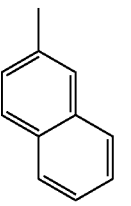 | direct bond | direct bond | 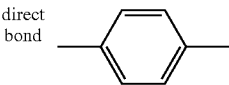 | H | H |
| 1-25 | 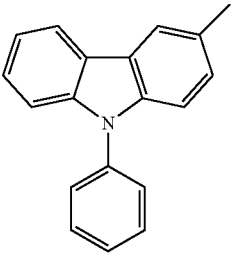 | 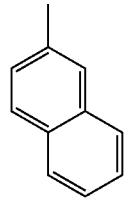 | 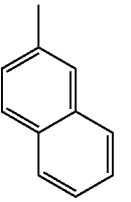 | direct bond | direct bond | direct bond | H | H |

TABLE 1-continued

| Formula | Ar | Ar₁ | Ar₂ | L₁ | L₂ | L₃ | X₁ | X₂ |
|---|---|---|---|---|---|---|---|---|
| 1-26 | carbazole-N-biphenyl | naphthyl | naphthyl | direct bond | direct bond | p-phenylene | H | H |
| 1-27 | 4,6-diphenylpyrimidin-2-yl | naphthyl | naphthyl | direct bond | direct bond | p-phenylene | H | H |
| 1-28 | phenanthridin-6-yl | naphthyl | naphthyl | direct bond | direct bond | p-phenylene | H | H |
| 1-29 | 4-phenylquinazolin-2-yl | naphthyl | naphthyl | direct bond | direct bond | p-phenylene | H | H |
| 1-30 | 2-(1-phenyl-1H-benzimidazol-2-yl)phenyl | naphthyl | naphthyl | direct bond | direct bond | direct bond | H | H |

TABLE 1-continued
| Formula | Ar | Ar₁ | Ar₂ | L₁ | L₂ | L₃ | X₁ | X₂ |
|---|---|---|---|---|---|---|---|---|
| 1-31 | 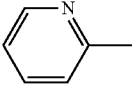 | 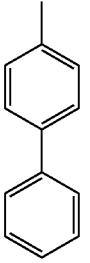 | 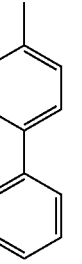 | direct bond | direct bond | 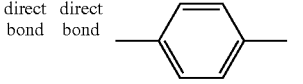 | H | H |
| 1-32 | 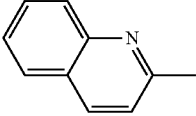 | 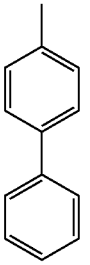 | 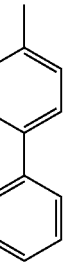 | direct bond | direct bond | 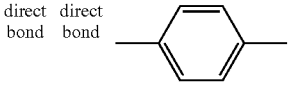 | H | H |
| 1-33 | 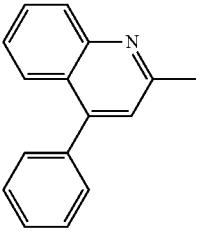 | 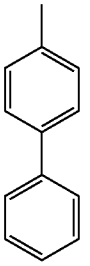 | 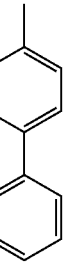 | direct bond | direct bond | 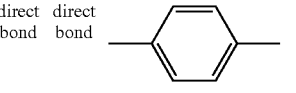 | H | H |
| 1-34 | 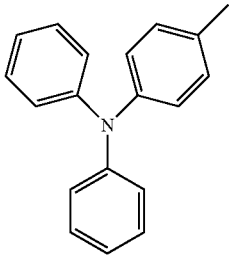 | 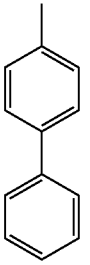 | 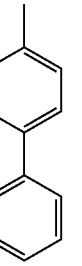 | direct bond | direct bond | 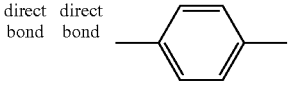 | H | H |
| 1-35 | 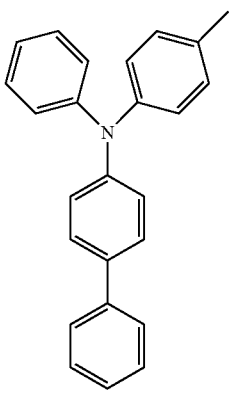 | 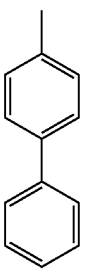 | 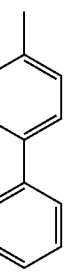 | direct bond | direct bond | 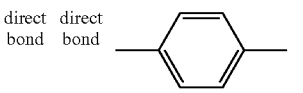 | H | H |

TABLE 1-continued
| Formula | Ar | Ar₁ | Ar₂ | L₁ | L₂ | L₃ | X₁ | X₂ |
|---|---|---|---|---|---|---|---|---|
| 1-36 | 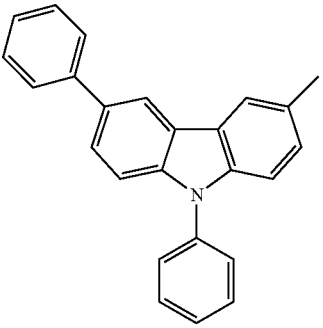 | 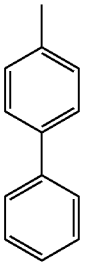 | 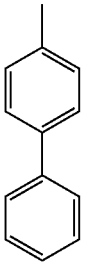 | direct bond | direct bond | 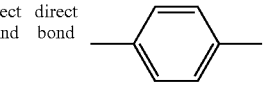 | H | H |
| 1-37 | 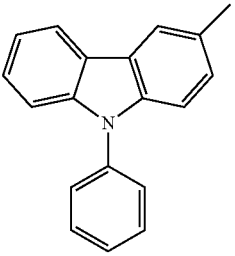 | 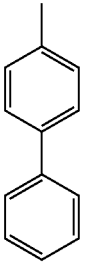 | 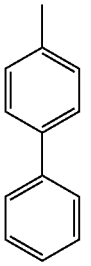 | direct bond | direct bond | 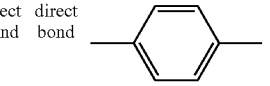 | H | H |
| 1-38 | 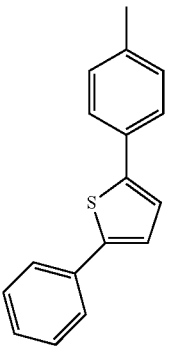 | 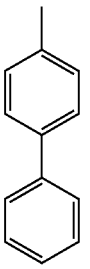 | 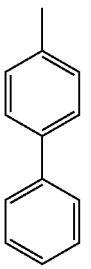 | direct bond | direct bond | 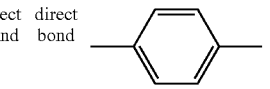 | H | H |
| 1-39 | 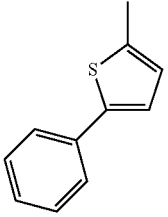 | 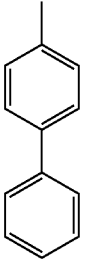 | 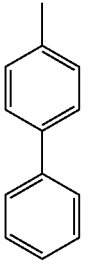 | direct bond | direct bond | 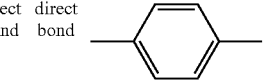 | H | H |
| 1-136 | 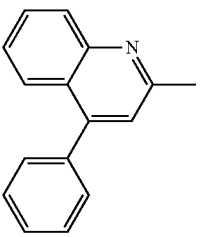 | 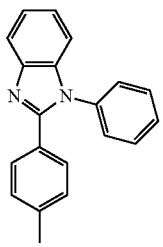 | 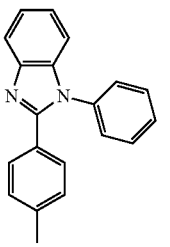 | direct bond | direct bond | 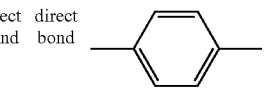 | H | H |

TABLE 1-continued

| Formula | Ar | Ar₁ | Ar₂ | L₁ | L₂ | L₃ | X₁ | X₂ |
|---|---|---|---|---|---|---|---|---|
| 1-137 | *N,N-diphenyl-N-methylamine* | phenyl | phenyl | direct bond | direct bond | direct bond | H | H |
| 1-138 | *N,N-diphenyl-N-methylamine* | phenyl | phenyl | direct bond | direct bond | phenylene | H | H |
| 1-139 | *stilbene-triphenylamine derivative* | phenyl | phenyl | direct bond | direct bond | phenylene | H | H |
| 1-140 | *N,N-diphenyl-N-methylamine* | *N,N-diphenylaminophenyl* | *N,N-diphenylaminophenyl* | direct bond | direct bond | direct bond | H | H |

In the compound that is represented by Formula 1, the compounds in which n is 2 are described in the following Table 1, but the scope of the present invention is not limited to the compounds described in the following Table 2.

TABLE 2

| Formula | Ar | Ar₁ | Ar₂ | L₁ | L₂ | L₃ | X₁ | X₂ |
|---|---|---|---|---|---|---|---|---|
| 1-40 | 1,4-phenylene | phenyl | phenyl | direct bond | direct bond | direct bond | H | H |
| 1-41 | 1,3-phenylene | phenyl | phenyl | direct bond | direct bond | direct bond | H | H |
| 1-42 | 1,5-naphthylene | phenyl | phenyl | direct bond | direct bond | direct bond | H | H |
| 1-43 | 2,6-naphthylene | phenyl | phenyl | direct bond | direct bond | direct bond | H | H |

TABLE 2-continued

| Formula | Ar | Ar₁ | Ar₂ | L₁ | L₂ | L₃ | X₁ | X₂ |
|---|---|---|---|---|---|---|---|---|
| 1-44 | 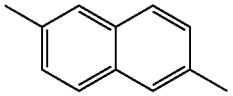 | 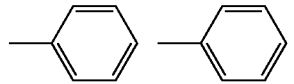 | 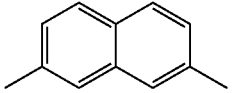 | direct bond | direct bond | direct bond | H | H |
| 1-45 | 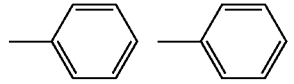 | | | direct bond | direct bond | direct bond | H | H |
| 1-46 | 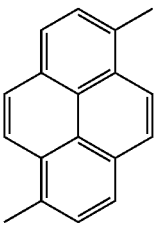 | | | direct bond | direct bond | direct bond | H | H |
| 1-47 | 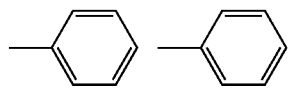 | | | direct bond | direct bond | direct bond | H | H |
| 1-48 | 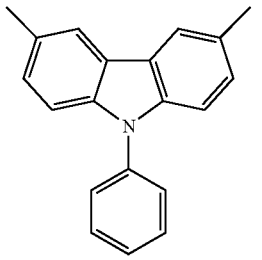 | 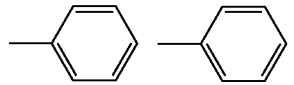 | 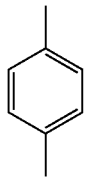 | direct bond | direct bond | direct bond | H | H |
| 1-49 | 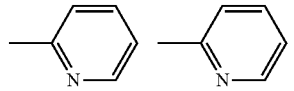 | | | direct bond | direct bond | direct bond | H | H |
| 1-50 | 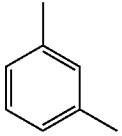 | | | direct bond | direct bond | direct bond | H | H |
| 1-51 | 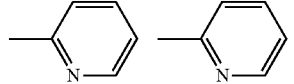 | | | direct bond | direct bond | direct bond | H | H |
| 1-52 | 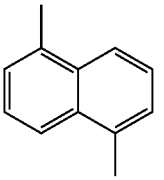 | | | direct bond | direct bond | direct bond | H | H |

| Formula | Ar | Ar₁ | Ar₂ | L₁ | L₂ | L₃ | X₁ | X₂ |
|---|---|---|---|---|---|---|---|---|
| 1-53 | 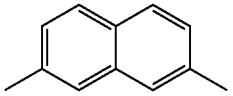 | 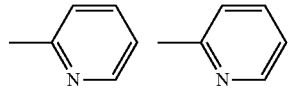 | 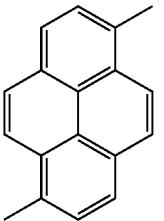 | direct bond | direct bond | direct bond | H | H |
| 1-54 | 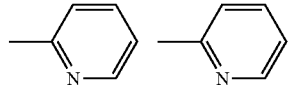 | 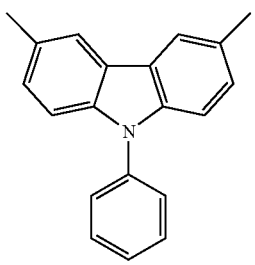 | 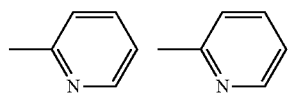 | direct bond | direct bond | direct bond | H | H |
| 1-55 | 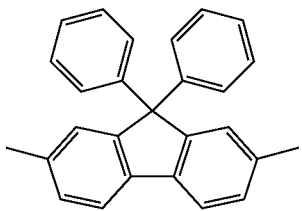 | 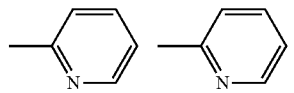 | 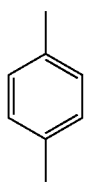 | direct bond | direct bond | direct bond | H | H |
| 1-56 | 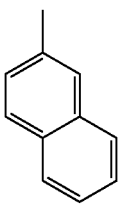 | 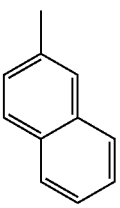 | 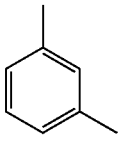 | direct bond | direct bond | direct bond | H | H |
| 1-57 | 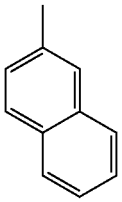 | 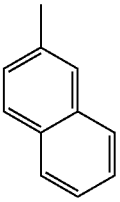 | 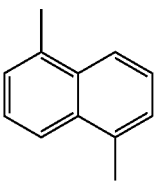 | direct bond | direct bond | direct bond | H | H |
| 1-58 | 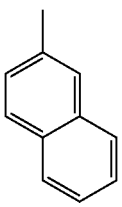 | | | direct bond | direct bond | direct bond | H | H |
| 1-59 | 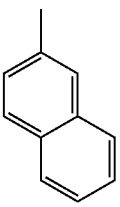 | | | direct bond | direct bond | direct bond | H | H |

TABLE 2-continued
| Formula | Ar | Ar₁ | Ar₂ | L₁ | L₂ | L₃ | X₁ | X₂ |
|---|---|---|---|---|---|---|---|---|
| 1-60 | 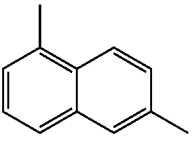 | 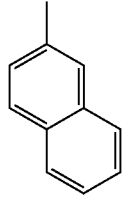 | 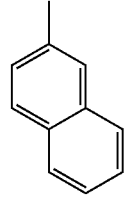 | direct bond | direct bond | direct bond | H | H |
| 1-61 | 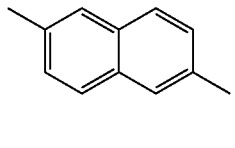 | 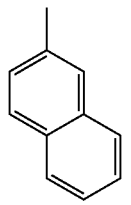 | 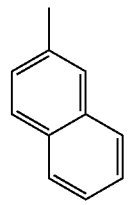 | direct bond | direct bond | direct bond | H | H |
| 1-62 | 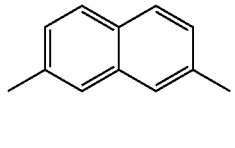 | 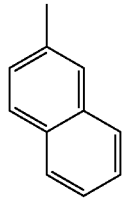 | 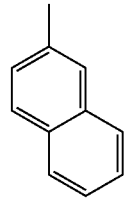 | direct bond | direct bond | direct bond | H | H |
| 1-63 | 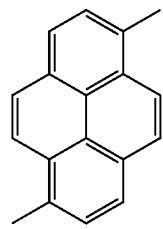 | 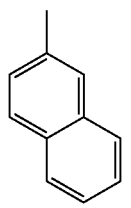 | 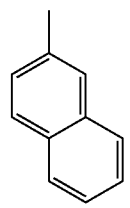 | direct bond | direct bond | direct bond | H | H |
| 1-64 | 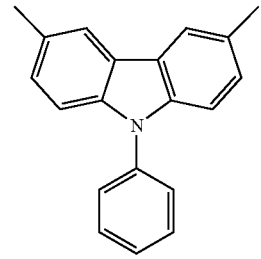 | 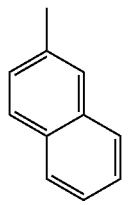 | 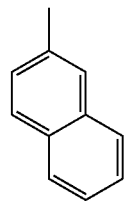 | direct bond | direct bond | direct bond | H | H |
| 1-65 | 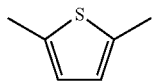 | 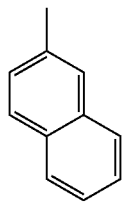 | 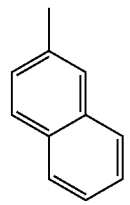 | direct bond | direct bond | direct bond | H | H |

TABLE 2-continued

| Formula | Ar | Ar₁ | Ar₂ | L₁ | L₂ | L₃ | X₁ | X₂ |
|---|---|---|---|---|---|---|---|---|
| 1-66 | 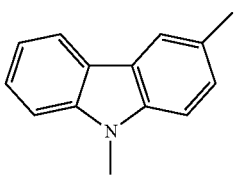 | 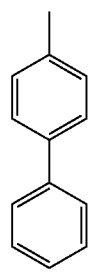 | 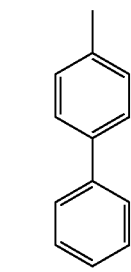 | direct bond | direct bond | 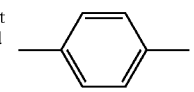 | H | H |

In the compound that is represented by Formula 1, the compounds in which n is 1, Ar₁ is —NAr₃Ar₄, and Ar₂ is —NAr₅Ar₆ are described in the following Table 3, but the scope of the present invention is not limited to the compounds described in the following Table 3.

TABLE 3

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-67 | 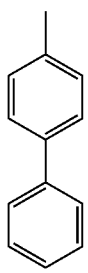 | 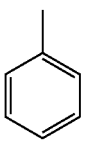 | 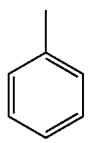 | 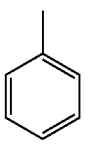 | 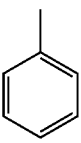 | direct bond | direct bond | direct bond | H | H |
| 1-68 | 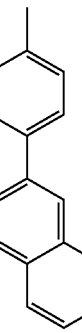 | 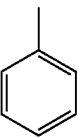 | 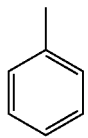 | 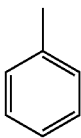 | 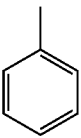 | direct bond | direct bond | direct bond | H | H |
| 1-69 | 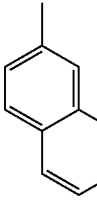 | 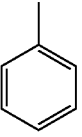 | 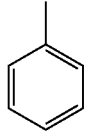 | 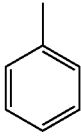 | 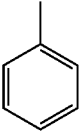 | direct bond | direct bond | direct bond | H | H |
| 1-70 | 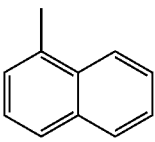 | 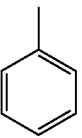 | 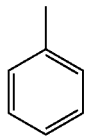 | 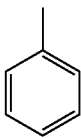 | 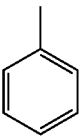 | direct bond | direct bond | direct bond | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-71 | 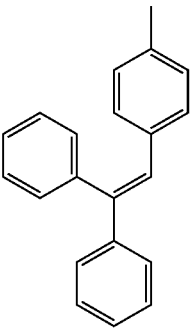 | 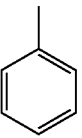 | 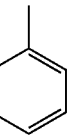 | 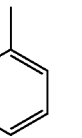 | 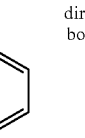 | direct bond | direct bond | direct bond | H | H |
| 1-72 | 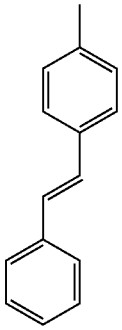 | 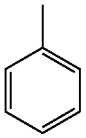 | 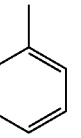 | 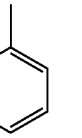 | 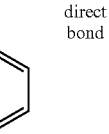 | direct bond | direct bond | direct bond | H | H |
| 1-73 |  | 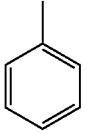 | 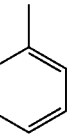 | 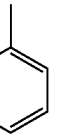 | 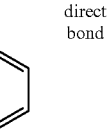 | direct bond | direct bond | direct bond | H | H |
| 1-74 | 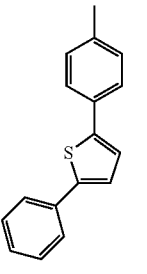 | 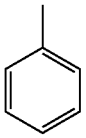 | 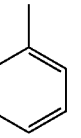 | 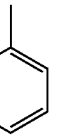 | 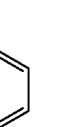 | direct bond | direct bond | direct bond | H | H |
| 1-75 | 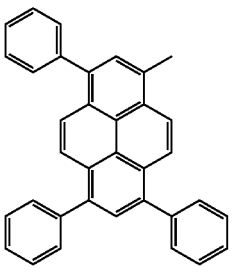 | 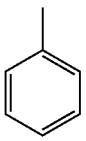 | 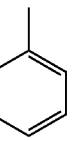 | 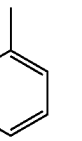 | 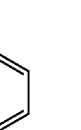 | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-76 | 2-methyl-9,10-diphenylanthracenyl | phenyl | phenyl | phenyl | phenyl | direct bond | direct bond | direct bond | H | H |
| 1-77 | 2-methyl-9,10-di(2-naphthyl)anthracenyl | phenyl | phenyl | phenyl | phenyl | direct bond | direct bond | direct bond | H | H |
| 1-78 | 4-(diphenylamino)phenyl | phenyl | phenyl | phenyl | phenyl | direct bond | direct bond | direct bond | H | H |
| 1-79 | 4-{N-phenyl-N-[4-(styryl)phenyl]amino}phenyl | phenyl | phenyl | phenyl | phenyl | direct bond | direct bond | direct bond | H | H |
| 1-80 | 4-[N,N-di(p-tolyl)amino]phenyl | phenyl | phenyl | phenyl | phenyl | direct bond | direct bond | direct bond | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-81 |  | 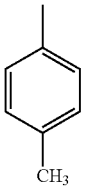 | 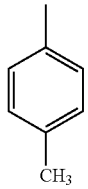 | 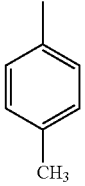 |  | direct bond | direct bond | direct bond | H | H |
| 1-82 | 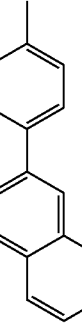 | 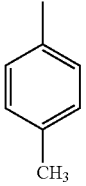 | 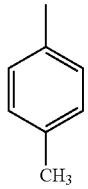 | 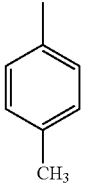 |  | direct bond | direct bond | direct bond | H | H |
| 1-83 | 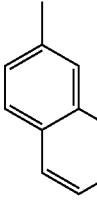 | 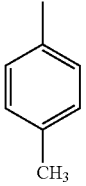 | 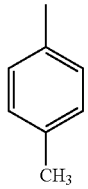 |  |  | direct bond | direct bond | direct bond | H | H |
| 1-84 | 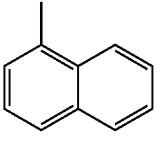 | 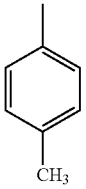 | 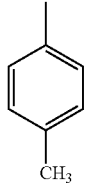 | 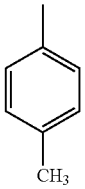 |  | direct bond | direct bond | direct bond | H | H |
| 1-85 | 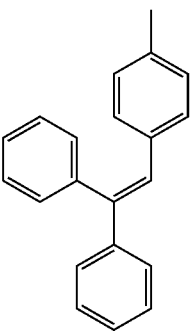 | 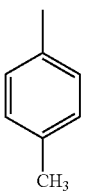 | 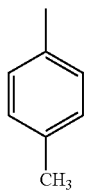 | 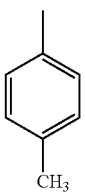 | 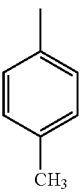 | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-86 | (stilbene-type structure with p-tolyl and phenyl) | p-tolyl | p-tolyl | p-tolyl | p-tolyl | direct bond | direct bond | direct bond | H | H |
| 1-87 | (9,9-diphenylfluorene-2-yl with methyl) | p-tolyl | p-tolyl | p-tolyl | p-tolyl | direct bond | direct bond | direct bond | H | H |
| 1-88 | (2,5-diaryl thiophene with p-tolyl and phenyl) | p-tolyl | p-tolyl | p-tolyl | p-tolyl | direct bond | direct bond | direct bond | H | H |
| 1-89 | (1,3,6-triphenylpyrene with methyl) | p-tolyl | p-tolyl | p-tolyl | p-tolyl | direct bond | direct bond | direct bond | H | H |
| 1-90 | (9,10-diphenylanthracen-2-yl with methyl) | p-tolyl | p-tolyl | p-tolyl | p-tolyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---------|----|----|----|----|----|----|----|----|----|----|
| 1-91 | 9,10-bis(2-naphthyl)-2-methylanthracene | p-tolyl | p-tolyl | p-tolyl | p-tolyl | direct bond | direct bond | direct bond | H | H |
| 1-92 | 4-methyl-triphenylamine | p-tolyl | p-tolyl | p-tolyl | p-tolyl | direct bond | direct bond | direct bond | H | H |
| 1-93 | N-phenyl-N-(4-methylphenyl)-4-styrylaniline | p-tolyl | p-tolyl | p-tolyl | p-tolyl | direct bond | direct bond | direct bond | H | H |
| 1-94 | tri(4-methylphenyl)amine | p-tolyl | p-tolyl | p-tolyl | p-tolyl | direct bond | direct bond | direct bond | H | H |
| 1-95 | 2-methylnaphthyl | 4-biphenylyl | 4-biphenylyl | 4-biphenylyl | 4-biphenylyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-96 | (stilbene-type structure with phenyl groups) | biphenyl | biphenyl | biphenyl | biphenyl | direct bond | direct bond | direct bond | H | H |
| 1-97 | (styryl-phenyl structure) | biphenyl | biphenyl | biphenyl | biphenyl | direct bond | direct bond | direct bond | H | H |
| 1-98 | (9,9-diphenylfluorene) | biphenyl | biphenyl | biphenyl | biphenyl | direct bond | direct bond | direct bond | H | H |
| 1-99 | (2,5-diphenylthiophene-phenyl) | biphenyl | biphenyl | biphenyl | biphenyl | direct bond | direct bond | direct bond | H | H |
| 1-100 | (triphenylpyrene) | biphenyl | biphenyl | biphenyl | biphenyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-101 | 9,10-diphenyl-2-anthryl | biphenyl | biphenyl | biphenyl | biphenyl | direct bond | direct bond | direct bond | H | H |
| 1-102 | 9,10-di(2-naphthyl)-2-anthryl | biphenyl | biphenyl | biphenyl | biphenyl | direct bond | direct bond | direct bond | H | H |
| 1-103 | 4-(diphenylamino)phenyl | biphenyl | biphenyl | biphenyl | biphenyl | direct bond | direct bond | direct bond | H | H |
| 1-104 | 4-[N-phenyl-N-(4-styrylphenyl)amino]phenyl | biphenyl | biphenyl | biphenyl | biphenyl | direct bond | direct bond | direct bond | H | H |
| 1-105 | 4-[bis(4-methylphenyl)amino]phenyl | biphenyl | biphenyl | biphenyl | biphenyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-106 | (2-naphthyl) | (phenyl) | (4-styryl-phenyl) | (phenyl) | (4-styryl-phenyl) | direct bond | direct bond | direct bond | H | H |
| 1-107 | (1,2,2-triphenylethenyl with p-tolyl) | (phenyl) | (4-styryl-phenyl) | (phenyl) | (4-styryl-phenyl) | direct bond | direct bond | direct bond | H | H |
| 1-108 | (5-phenyl-2-thienyl with p-tolyl) | (phenyl) | (4-styryl-phenyl) | (phenyl) | (4-styryl-phenyl) | direct bond | direct bond | direct bond | H | H |
| 1-109 | (1,3,6-triphenylpyrenyl) | (phenyl) | (4-styryl-phenyl) | (phenyl) | (4-styryl-phenyl) | direct bond | direct bond | direct bond | H | H |
| 1-110 | (9,10-diphenylanthracen-2-yl) | (phenyl) | (4-styryl-phenyl) | (phenyl) | (4-styryl-phenyl) | direct bond | direct bond | direct bond | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-111 | 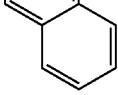 |  |  |  |  |  |  | direct bond | H | H |
| 1-112 | 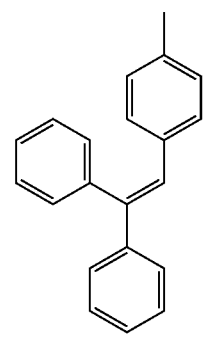 | 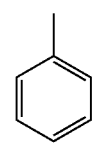 | 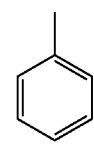 | 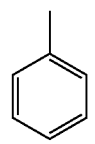 | 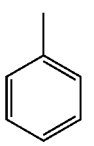 | 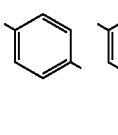 | 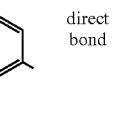 | direct bond | H | H |
| 1-113 | 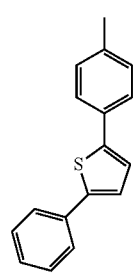 | 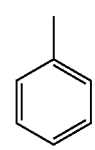 | 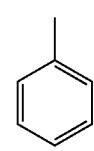 | 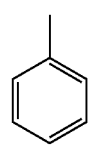 | 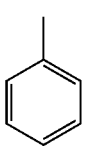 | 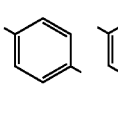 | 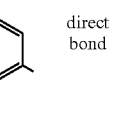 | direct bond | H | H |
| 1-114 | 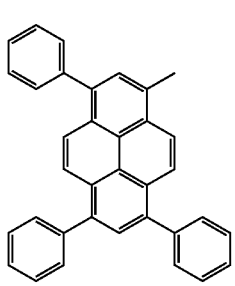 | 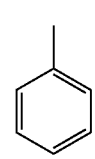 | 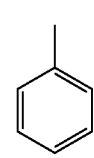 | 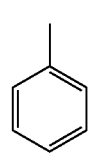 | 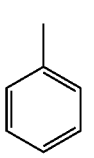 | 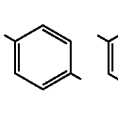 | 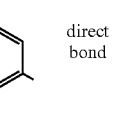 | direct bond | H | H |
| 1-115 | 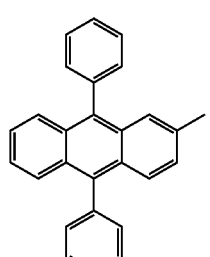 | 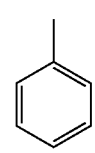 | 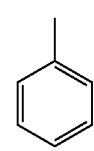 | 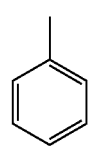 | 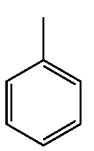 | 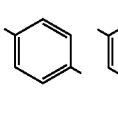 | 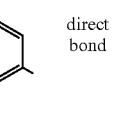 | direct bond | H | H |
| 1-116 | 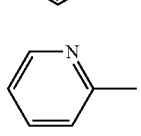 | 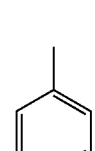 | 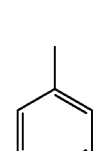 | 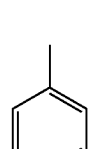 | 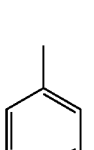 | 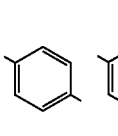 | 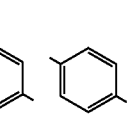 | | H | H |

US 9,012,040 B2
51 52
TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-117 | 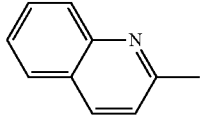 | 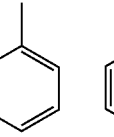 | 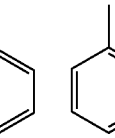 | 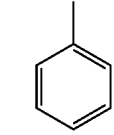 | 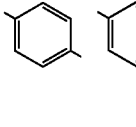 | 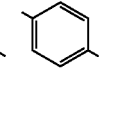 |  |  | H | H |
| 1-118 | 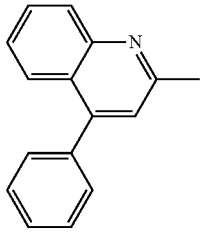 | 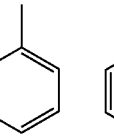 | 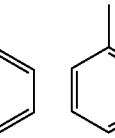 | 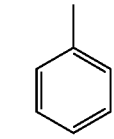 | 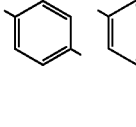 | 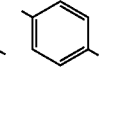 |  |  | H | H |
| 1-119 | 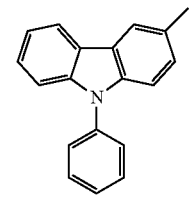 | 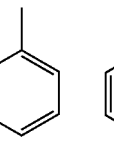 | 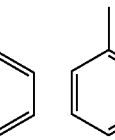 | 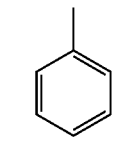 | 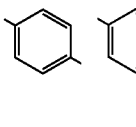 | 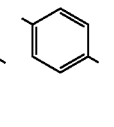 | 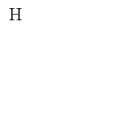 | 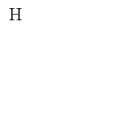 | H | H |
| 1-120 | 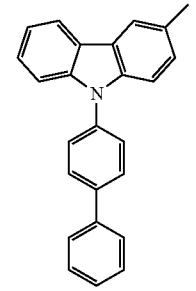 | 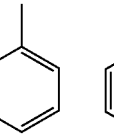 | 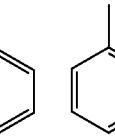 | 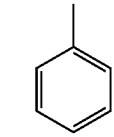 | 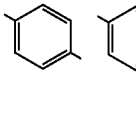 | 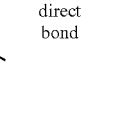 | 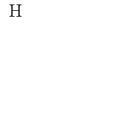 | direct bond | H | H |
| 1-121 | 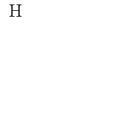 | 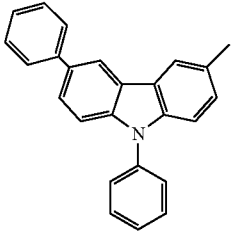 | 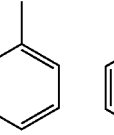 | 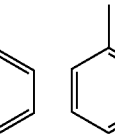 | 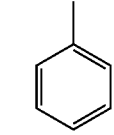 | 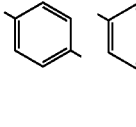 | 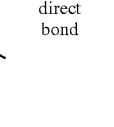 | direct bond | H | H |
| 1-122 |  |  | 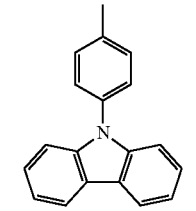 | 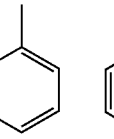 | 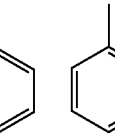 | 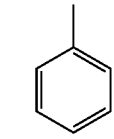 | 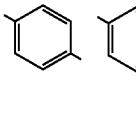 | 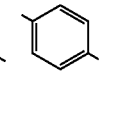 | H | H |
| 1-123 |  |  | 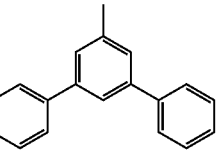 | 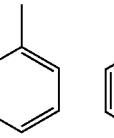 | 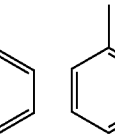 | 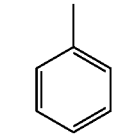 | 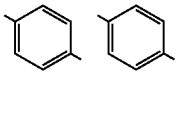 | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-124 | 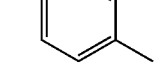 |  |  |  |  | 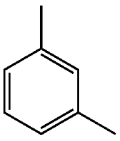 | 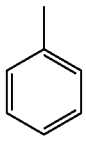 | direct bond | H | H |
| 1-125 | 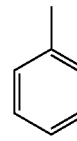 | 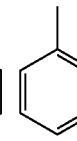 | 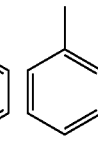 | 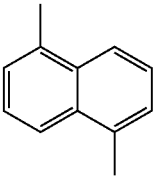 | 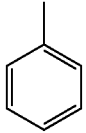 | 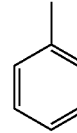 | 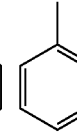 | 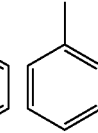 | H | H |
| 1-141 | 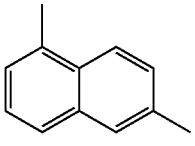 | 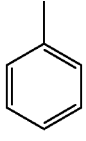 | 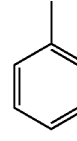 | 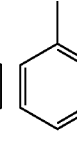 | 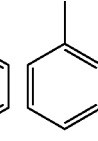 | direct bond | direct bond | direct bond | H | H |

In the compound that is represented by Formula 1, the compounds in which n is 2, Ar₁ is —NAr₃Ar₄, and Ar₂ is —NAr₅Ar₆ are described in the following Table 4, but the scope of the present invention is not limited to the compounds described in the following Table 4.

TABLE 4

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-126 | 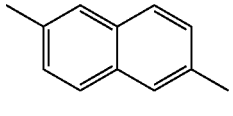 | 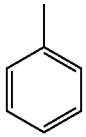 | 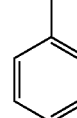 | 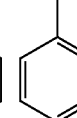 | 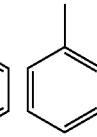 | direct bond | direct bond | direct bond | H | H |
| 1-127 | | | | | | direct bond | direct bond | direct bond | H | H |
| 1-128 | | | | | | direct bond | direct bond | direct bond | H | H |
| 1-129 | | | | | | direct bond | direct bond | direct bond | H | H |
| 1-130 | | | | | | direct bond | direct bond | direct bond | H | H |

TABLE 4-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-131 | naphthalene-2,6-diyl | phenyl | phenyl | phenyl | phenyl | direct bond | direct bond | direct bond | H | H |
| 1-132 | pyrene-1,6-diyl | phenyl | phenyl | phenyl | phenyl | direct bond | direct bond | direct bond | H | H |
| 1-133 | 9-phenylcarbazole-3,6-diyl | phenyl | phenyl | phenyl | phenyl | direct bond | direct bond | direct bond | H | H |
| 1-134 | thiophene-2,5-diyl | phenyl | phenyl | phenyl | phenyl | direct bond | direct bond | direct bond | H | H |
| 1-135 | 3,3'-biphenyl-diyl | phenyl | phenyl | phenyl | phenyl | direct bond | direct bond | direct bond | H | H |

The anthracene derivative that is represented by Formula 1 according to the present invention can be synthesized by using a known synthesis method such as a Suzuki coupling reaction. The more detailed preparation method is described in the following Preparative Examples, and the compound according to the present invention can be prepared by modifying the detailed examples described in the following Preparative Examples by those who are skilled in the art.

The organic electron device according to the present invention is characterized in that it uses the anthracene derivative that is represented by Formula 1.

The organic electronic device of the present invention can be prepared by usual methods and materials for preparing an organic electronic device, except that the above-described compounds are used to form at least one organic material layer. Hereinafter, the organic light emitting device will be described.

The above-mentioned compounds according to the present invention can act as the light emitting material in the organic light emitting device, and can act as the light emitting host in conjunction with a predetermined light emitting dopant, or can act as the light emitting dopant in conjunction with a predetermined light emitting host.

In one embodiment of the present invention, the organic light emitting device can have a structure comprising a first electrode, a second electrode, and organic material layers interposed therebetween. The organic light emitting device of the present invention can be prepared by usual methods and materials for preparing an organic light emitting device, except that the compounds according to the present invention are used to form at least one of the organic material layers of the organic light emitting device. The structure of the organic light emitting device according to the present invention is shown in FIG. 1.

For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer and an electron transporting layer on the anode; and depositing a material, which can be used as a cathode, thereon. Alternatively, an organic light emitting device can be prepared by sequentially depositing a cathode material, an organic material layer, and an anode material on a substrate, thus preparing the above-described organic light emitting device.

The organic material layer may have a multilayered structure that comprises the hole injection layer, the hole transport layer, the light emitting layer and the electron transport layer, but is not limited thereto, and the organic material layer may have a single layer structure. Further, the organic material layer can be prepared to have a fewer number of layers, using a variety of polymeric materials, by means of a solvent process rather than a deposit process, such as spin coating, dip coating, doctor blading, screen printing, ink jet printing, or heat transfer processes.

The anode material is preferably a material having a large work function to facilitate hole injection usually to the organic material layers. Specific examples of the anode material which can be used in the present invention comprise metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide, such as ZnO:Al and SnO$_2$:Sb; conductive polymers such as poly(3-methylthiophene), poly[3,4-(ethylene-1,2-dioxy)thiophene] (PEDT), polypyrrole and polyaniline, but are not limited thereto.

The cathode material is preferably a material having a small work function to facilitate electron injecting usually to an organic material layer. Specific examples of the cathode material comprise metals such as magnesium, calcium, sodium, potassium, titanium, indium, yttrium, lithium, gadolinium, aluminum, silver, tin and lead, and an alloy thereof; and multilayered materials such as LiF/Al and LiO$_2$/Al, but are not limited thereto.

The hole injecting material is a material facilitating hole injection from an anode at low voltage. The HOMO (highest occupied molecular orbital) of the hole injecting material is preferably located between the work function of the anode materials and the HOMO level of its neighboring organic material layer. Specific examples of the hole injecting material comprise organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is a material having high hole mobility, which can transfer holes from the anode or the hole injecting layer toward the light emitting layer. Specific examples thereof comprise organic materials of arylamine series, conductive polymers and block copolymers having both of the conjugated portions and the non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof comprise 8-hydroxyquinoline aluminum complex (Alq$_3$); compounds of carbazole series; dimerized styryl compounds; BAlq; 10-hydroxyberizoquinoline-metal compounds; compounds of benzoxazole, benzthiazole and benzimidazole series; polymers of poly(p-phenylenevinylene) (PPV) series; spiro compounds; and polyfluorene and rubrene compounds, but are not limited thereto.

The electron transporting material is suitably a material having high electron mobility, which can easily receive electrons from the cathode and then transfer them to the light emitting layer. Specific examples thereof comprise an Al complex of an 8-hydroxyquinoline; complexes comprising Alq$_3$; organic radical compounds; and hydroxyflavone-metal complexes, but are not limited thereto.

The organic light emitting device according to the present invention may be of a front-sided, back-sided or double-sided light emission according to the materials used.

The compound according to the invention can also function in an organic electronic device comprising an organic solar cell, an organic photoconductor and an organic transistor, according to a principle similar to that applied to the organic light emitting device.

MODE FOR INVENTION

Hereinafter, preferable Examples are provided for the purpose of making the present invention more understandable. As such, Examples are provided for illustrating the Examples, but the scope of the invention is not limited thereto.

The compound that is represented by Formula 1 according to the present invention can be prepared by using a multistage chemical reaction. The preparation of the compounds is described in the following Examples. The compound according to the present invention can be prepared from an intermediate compound such as the following intermediate compounds A to W. In these compounds, "Br" and "Cl" can be substituted by predetermined other reactive atoms or functional groups.

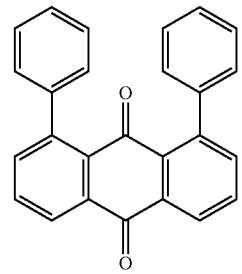

[compound A]

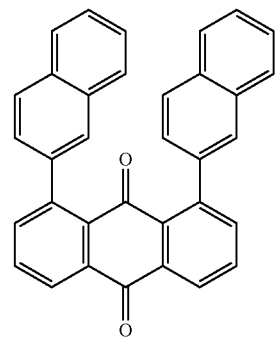

[compound B]

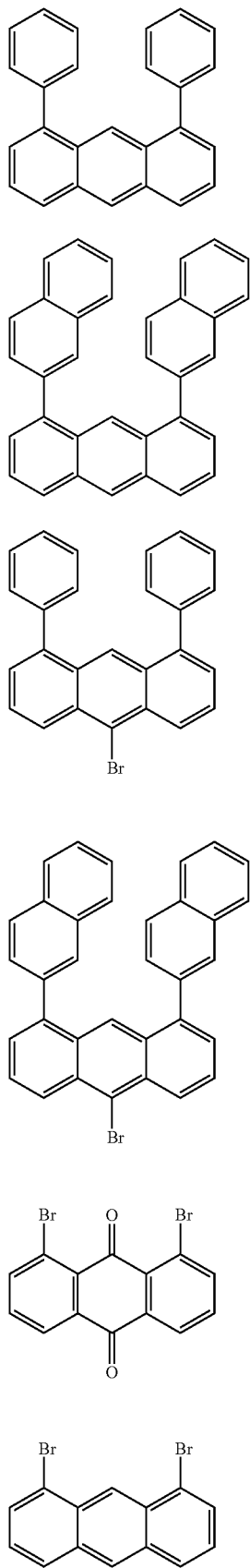
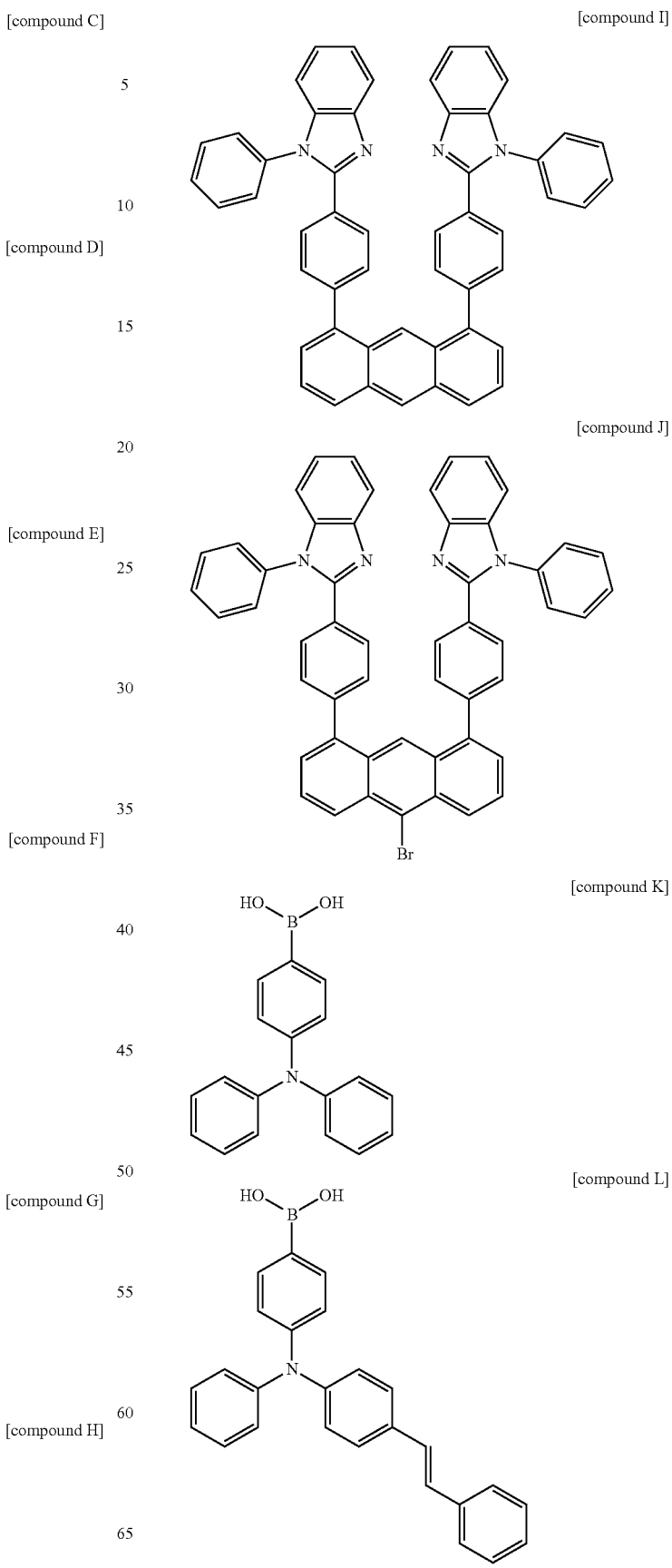

[compound M]
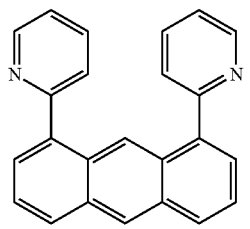
[compound N]
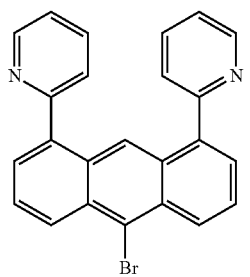
[compound O]
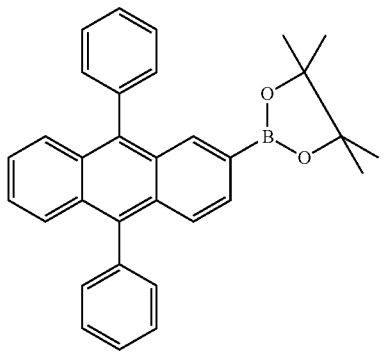
[compound P]
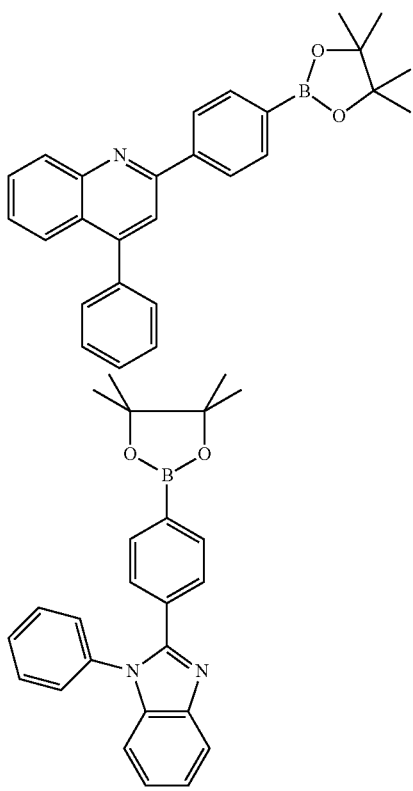
[compound Q]
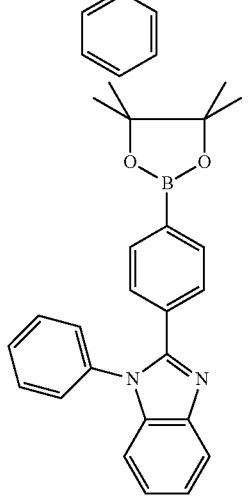
[compound R]
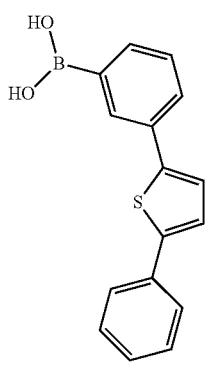
[compound S]
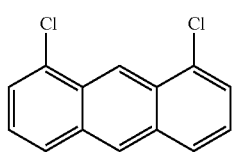
[compound T]
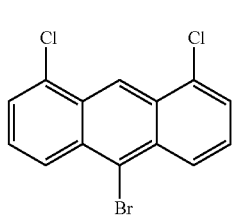
[compound U]
[compound V]

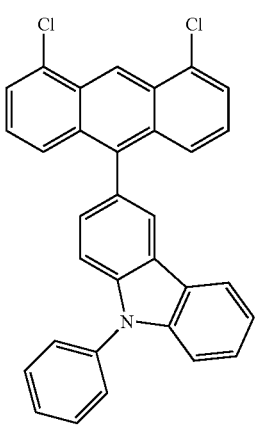

[compound W]

Preparative Example 1

Preparation of the Compound A

Under nitrogen, 1,8-dichloroanthraquinone (50 g, 0.18 mol), phenyl boronic acid (48 g, 0.4 mol), Pd(PPh$_3$)$_4$ (6.3 g, 2.17 mmol) were put into the 2 M K$_2$CO$_3$ aqueous solution (200 mL) and THF (400 mL), and refluxed and agitated for about 12 hours. After the reaction was finished, it was cooled to normal temperature, and the organic layer was separated from the reaction mixture solution, dried with magnesium sulfate, distilled under reduced pressure, and recrystallized with THF/EtOH to obtain the compound A (47 g, 72%).

MS [M]=360

Preparative Example 2

Preparation of the Compound B

Under nitrogen, 1,8-dichloroanthraquinone (20 g, 72.2 mol), 2-naphthalene boronic acid (27.3 g, 158 mmol), Pd(PPh$_3$)$_4$ (2.5 g, 2.17 mmol) were put into the 2 M K$_2$CO$_3$ aqueous solution (100 mL) and THF (500 mL), and refluxed and agitated for about 12 hours. After the reaction was finished, it was cooled to normal temperature, and the organic layer was separated from the reaction mixture solution, dried with magnesium sulfate, distilled under reduced pressure, and recrystallized with THF/EtOH to obtain the compound B (17 g, 52%).

MS [M]=460

Preparative Example 3

Preparation of the Compound C

Under nitrogen, the compound A (11.2 g, 20.5 mmol) that was prepared in Preparative Example 1 was dispersed in the acetic acid (200 mL), 57% HI (500 mL) and 50% H$_3$PO$_2$ (250 mL) were added thereto, and they were boiled for 4 days and agitated. After they were cooled to normal temperature, the layer separation was carried out by using chloroform, the organic layer was dried with magnesium sulfate, distilled under reduced pressure, and recrystallized with EtOH to obtain the compound C (58 g, 65%).

MS [M]=330

Preparative Example 4

Preparation of the Compound D

Under nitrogen, the compound B (16 g, 34.7 mmol) that was prepared in Preparative Example 2 was dispersed in the acetic acid (750 mL), 57% HI (100 mL) and 50% H$_3$PO$_2$ (50 mL) were added thereto, and they were refluxed and agitated for 3 days. After the reaction was finished, they were cooled to normal temperature, and the solid that was generated in the reaction was filtered, dissolved in chloroform, and treated with magnesium sulfate. This organic layer was distilled under reduced pressure, and recrystallized with EtOH to obtain the yellow solid compound D (7.96 g, 53%).

MS [M]=430

Preparative Example 5

Preparation of the Compound E

Under nitrogen, the compound C (11.6 g, 35 mmol) that was prepared in Preparative Example 3 was dissolved in chloroform (200 mL), NBS (6.25 g, 35 mmol) was added thereto, and they were agitated at room temperature for 12 hours. After the reaction was finished, the solid that was generated in the reaction was filtered, washed with distilled water, and dried to obtain the compound E (5 g, 36%).

MS [M]=409

Preparative Example 6

Preparation of the Compound F

Under nitrogen, the compound D (7.96 g, 18.48 mmol) that was prepared in Preparative Example 4 was dissolved in chloroform (400 mL), NBS (3.3 g, 18.48 mmol) was added thereto, and they were agitated at room temperature for 12 hours. After the reaction was finished, the solid that was generated in the reaction was filtered, washed with distilled water, and dried to obtain the compound F (5 g, 55%).

MS [M]=509

Preparative Example 7

Preparation of the Compound G

Under nitrogen, 1,8-dichloroanthraquinone (2.0 g, 7.0 mmol), KBr (4.0 g, 33.6 mmol), CuCl$_2$ (0.1 g, 0.7 mmol), and 85% H$_3$PO$_4$ (4 mL) were dissolved in nitrobenzene (15 mL). After water was distilled from the solution until the temperature of the reaction mixture solution was 200° C., the reaction mixture solution was refluxed and agitated for 24 hours. After the reaction was finished, it was cooled to normal temperature, and methanol was put thereinto, thus carrying out the precipitation. It was purified with the column chromatography and dried to obtain the compound G (1.3 g, 45%).

MS [M]=336

Preparative Example 8

Preparation of the Compound H

Under nitrogen, the compound G (7.5 g, 20.5 mmol) that was prepared in Preparative Example 7 was dispersed in the acetic acid (200 mL), 57% HI (500 mL) and 50% H$_3$PO$_2$ (250 mL) were added thereto, and they were boiled for 4 days and agitated. After they were cooled to normal temperature, the layer separation was carried out by using chloroform, the organic layer was dried with magnesium sulfate, distilled under reduced pressure, and recrystallized with EtOH to obtain the compound H (4.42 g, 65%).

MS [M]=336

Preparative Example 9

Preparation of the Compound I

Under nitrogen, the compound H (4 g, 11.9 mmol) that was prepared in Preparative Example 8, the compound Q (9.9 g, 24.9 mmol), Pd(PPh$_3$)$_4$ (0.4 g, 0.36 mmol) were put into the 2 M K$_2$CO$_3$ aqueous solution (40 mL) and THF (80 mL), and refluxed and agitated for about 12 hours. After the reaction was finished, it was cooled to normal temperature, and the organic layer was separated from the reaction mixture solution, dried with magnesium sulfate, distilled under reduced pressure, and recrystallized with THF/EtOH to obtain the compound I (6.9 g, 82%).

MS [M]=714

Preparative Example 10

Preparation of the Compound J

Under nitrogen, the compound I (6.9 g, 9.66 mmol) that was prepared in Preparative Example 9 was dissolved in chloroform (500 mL), NBS (1.7 g, 18.48 mmol) was added thereto, and they were agitated at room temperature for 12 hours. After the reaction was finished, the solid that was generated in the reaction was filtered, washed with distilled water, and dried to obtain the compound J (3.8 g, 50%).

MS [M]=793

Preparative Example 11

Preparation of the Compound M

Under nitrogen, the compound H (4 g, 11.9 mmol) that was prepared in Preparative Example 8, 2-pyridin boronic acid (3.0 g, 24.9 mmol), and Pd(PPh$_3$)$_4$ (0.4 g, 0.36 mmol) were put into the 2 M K$_2$CO$_3$ aqueous solution (40 mL) and THF (80 mL), and refluxed and agitated for about 12 hours. After the reaction was finished, it was cooled to normal temperature, and the organic layer was separated from the reaction mixture solution, dried with magnesium sulfate, distilled under reduced pressure, and recrystallized with THF/EtOH to obtain the compound M (3.2 g, 80%).

MS [M]=332

Preparative Example 12

Preparation of the Compound N

Under nitrogen, the compound M (3.21 g, 9.66 mmol) that was prepared in Preparative Example 11 was dissolved in chloroform (300 mL), NBS (1.7 g, 18.48 mmol) was added thereto, and they were agitated at room temperature for 12 hours. After the reaction was finished, the solid that was generated in the reaction was filtered, washed with distilled water, and dried to obtain the compound N (2.0 g, 50%).

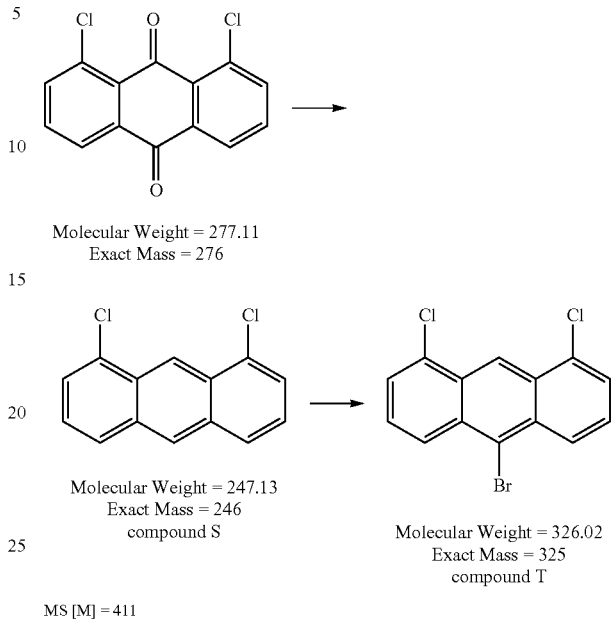

Preparative Example 13

Preparation of the Compound S

Under nitrogen, 1,8-dichloroanthraquinone (10 g, 36 mmol) was dissolved in ammonia water (200 mL), and Zn dust (500 g) was added thereto, and they were refluxed and agitated. After the reaction was finished, they were cooled to normal temperature, and filtered, and the organic layer was separated from the reaction solution, dried with magnesium sulfate, distilled under reduced pressure, and recrystallized with hexane to obtain a solid. The obtained solid was dissolved in isopropyl alcohol, conc.-hydrochloric acid was put thereinto, and it was refluxed and agitated for 5 hours. After the reaction was finished, it was cooled to normal temperature, and the generated solid was filtered, rinsed with water, and dried to obtain the compound S (5.56 g, 63%).

MS [M]=246

Preparative Example 14

Preparation of the Compound T

Under nitrogen, the compound S (5.56 g, 22.5 mmol) that was prepared in Preparative Example 13 was dissolved in chloroform (200 mL), NBS (4.2 g, 24 mmol) was added thereto, and they were agitated at room temperature for 12 hours. After the reaction was finished, the solid that was generated in the reaction was filtered, washed with distilled water, and dried to obtain the compound T (2.3 g, 30%).

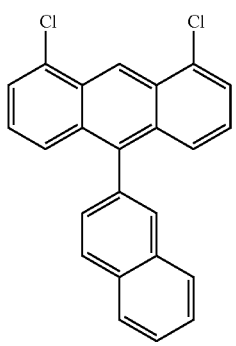

Formula U

Molecular Weight = 373.29
Exact Mass = 372

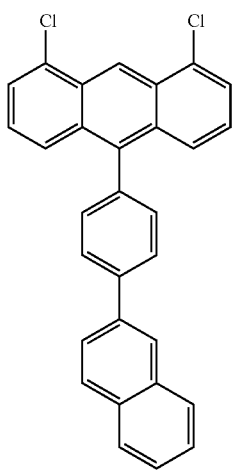

Formula V

Molecular Weight = 449.38
Exact Mass = 448

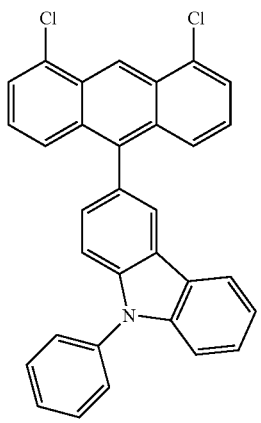

Formula W

Molecular Weight = 448.42
Exact Mass = 487
MS [M] = 325

Preparative Example 15

Preparation of the Compound U

Under nitrogen, the compound T (2.3 g, 7.05 mmol) that was prepared in Preparative Example 14, 2-naphthalene boronic acid (1.33 g, 7.76 mmol), and $Pd(PPh_3)_4$ (0.24 g, 0.21 mmol) were put into the 2 M $K_2CO_3$ aqueous solution (40 mL) and THF (80 mL), and refluxed and agitated for about 12 hours. After the reaction was finished, it was cooled to normal temperature, and the organic layer was separated from the reaction mixture solution, and filtered to obtain a solid. The obtained solid was recrystallized with THF and ethanol to obtain the compound U (2.2 g, 85%).

MS [M+H]+=372

Preparative Example 16

Preparation of the Compound V

Under nitrogen, the compound T (2.3 g, 7.05 mmol) that was prepared in Preparative Example 14, 4-(naphthalenyl-3) phenyl boronic acid (1.92 g, 7.76 mmol), and $Pd(PPh_3)_4$ (0.24 g, 0.21 mmol) were put into the 2 M $K_2CO_3$ aqueous solution (40 mL) and THF (80 mL), and refluxed and agitated for about 12 hours. After the reaction was finished, it was cooled to normal temperature, and the organic layer was separated from the reaction mixture solution, and filtered to obtain a solid. The obtained solid was recrystallized with THF and ethanol to obtain the compound V (2.65 g, 84%).

MS [M+H]+=448

Preparative Example 17

Preparation of the Compound W

Under nitrogen, the compound T (2.3 g, 7.05 mmol) that was prepared in Preparative Example 14, 3-(4,4,5,5-tetramethyl-1,3,2-dioxaboranyl-2)-9-phenyl-9H-carbazole (2.86 g, 7.76 mmol), and $Pd(PPh_3)_4$ (0.24 g, 0.21 mmol) were put into the 2 M $K_2CO_3$ aqueous solution (40 mL) and THF (80 mL), and refluxed and agitated for about 12 hours. After the reaction was finished, it was cooled to normal temperature, and the organic layer was separated from the reaction mixture solution, and filtered to obtain a solid. The obtained solid was recrystallized with THF and ethanol to obtain the compound W (2.95 g, 86%).

MS [M+H]+=487

Example 1

Preparation of the Compound 1-69

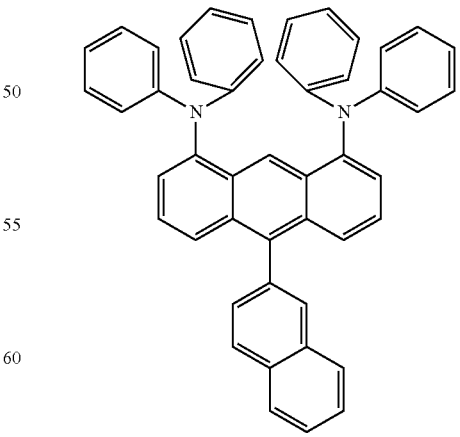

Molecular Weight = 638.82
Exact Mass = 638

Under nitrogen, the compound U (2.2 g, 5.89 mmol) that was prepared in Preparative Example 15, diphenylamine (2.09 g, 12.38 mmol), pd(dba)$_2$ (0.097 g, 0.17 mmol), P(t-Bu)$_3$ (0.05 g, 0.255 mmol) and sodium t-butoxide (2.45 g, 25.5 mmol) were put into toluene (100 mL), and refluxed for about 5 hours. After the reaction was finished, it was cooled to normal temperature, the reaction mixture solution was put into the mixture solution of THF and H$_2$O. The organic layer was separated, and the solution was dried with MgSO$_4$, and concentrated. It was purified with the column chromatography to obtain the compound 1-69 (3 g, 80%).

MS [M]=638

Example 2

Preparation of the Compound 1-68

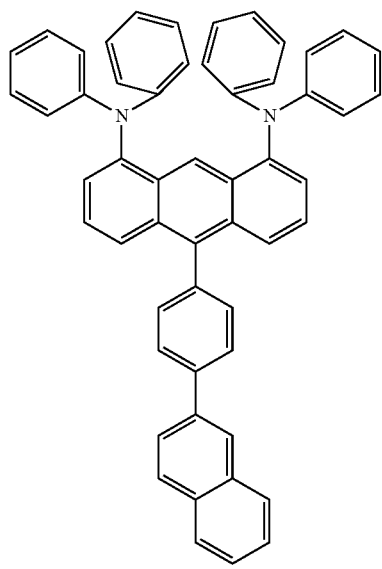

Molecular Weight = 714.92
Exact Mass = 714

Under nitrogen, the compound V (2.6 g, 5.89 mmol) that was prepared in Preparative Example 16, diphenylamine (2.09 g, 12.38 mmol), pd(dba)$_2$ (0.097 g, 0.17 mmol), P(t-Bu)$_3$ (0.05 g, 0.255 mmol) and sodium t-butoxide (2.45 g, 25.5 mmol) were put into toluene (100 mL), and refluxed for about 5 hours. After the reaction was finished, it was cooled to normal temperature, the reaction mixture solution was put into the mixture solution of THF and H$_2$O. The organic layer was separated, and the solution was dried with MgSO$_4$, and concentrated. It was purified with the column chromatography to obtain the compound 1-68 (3.1 g, 75%).

MS [M]=714

Example 3

Preparation of the Following Compound

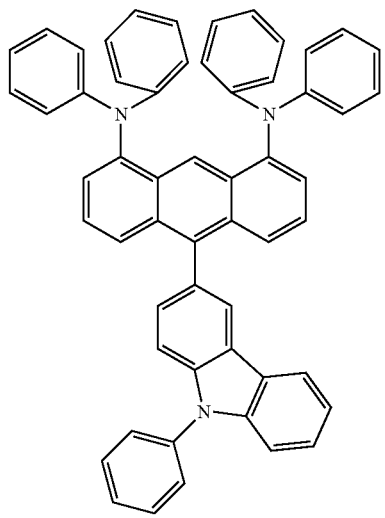

Molecular Weight = 753.96
Exact Mass = 753

Under nitrogen, the compound W (2.9 g, 5.89 mmol) that was prepared in Preparative Example 17, diphenylamine (2.09 g, 12.38 mmol), pd(dba)$_2$ (0.097 g, 0.17 mmol), P(t-Bu)$_3$ (0.05 g, 0.255 mmol) and sodium t-butoxide (2.45 g, 25.5 mmol) were put into toluene (100 mL), and refluxed for about 5 hours. After the reaction was finished, it was cooled to normal temperature, the reaction mixture solution was put into the mixture solution of THF and H$_2$O. The organic layer was separated, and the solution was dried with MgSO$_4$, and concentrated. It was purified with the column chromatography to obtain the compound (3.4 g, 76%).

MS [M]=753

Example 4

Preparation of the Compound 1-8

Under nitrogen, the compound E (4 g, 9.7 mmol) that was prepared in Preparative Example 5, 3-(4,4,5,5-tetramethyl-1,3,2-dioxaboranyl-2)-9-phenyl-9H-carbazole (3.6 g, 10 mmol), and Pd(PPh$_3$)$_4$ (0.3 g, 0.29 mmol) were put into the 2M K$_2$CO$_3$ aqueous solution (80 mL) and THF (120 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-8 (3.8 g, 86%).

MS [M+H]+=571

Example 5

Preparation of the Compound 1-21

Under nitrogen, the compound F (4 g, 7.8 mmol) that was prepared in Preparative Example 6, the compound R (2.3 g, 8.0 mmol), and Pd(PPh$_3$)$_4$ (0.3 g, 0.29 mmol) were put into the 2M K$_2$CO$_3$ aqueous solution (80 mL) and THF (120 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-21 (3.8 g, 86%).

MS [M+H]+=664

Example 6

Preparation of the Compound 1-24

Under nitrogen, the compound F (6.1 g, 12 mmol) that was prepared in Preparative Example 6, the compound P (4.9 g, 12 mmol), and Pd(PPh$_3$)$_4$ (0.3 g, 0.29 mmol) were put into the 2M. K$_2$CO$_3$ aqueous solution (80 mL) and THF (200 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-24 (5.2 g, 70%).

MS [M+H]+=709

Example 7

Preparation of the Compound 1-136

Under nitrogen, the compound J (4.0 g, 9.8 mmol) that was prepared in Preparative Example 10, the compound P (4.4 g, 10.79 mmol), and Pd(PPh$_3$)$_4$ (0.3 g, 0.29 mmol) were put into the 2M K$_2$CO$_3$ aqueous solution (80 mL) and THF (200 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-136 (5.2 g, 80%).

MS [M+H]+=993

Example 8

Preparation of the Compound 1-137

Under nitrogen, the compound E (4 g, 9.7 mmol) that was prepared in Preparative Example 5, diphenylamine (2.09 g, 12.38 mmol), pd(dba)$_2$ (0.097 g, 0.17 mmol), P(t-Bu)$_3$ (0.05 g, 0.255 mmol) and sodium t-butoxide (2.45 g, 25.5 mmol) were put into toluene (100 mL), and refluxed for about 5 hours. After the reaction was finished, it was cooled to normal temperature, and the reaction mixture solution was put into the mixture solution of THF and H$_2$O. The organic layer was separated, dried with MgSO$_4$, and concentrated. It was purified with the column chromatography to obtain the compound 1-137 (3 g, 80%).

MS [M]=497

Example 9

Preparation of the Compound 1-138

Under nitrogen, the compound E (4 g, 9.7 mmol) that was prepared in Preparative Example 5, the compound K (5.9 g, 10.75 mmol), and Pd(PPh$_3$)$_4$ (0.3 g, 0.29 mmol) were put into the 2M K$_2$CO$_3$ aqueous solution (80 mL) and THF (120 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-138 (8.2 g, 85%).

MS [M+H]+=810

Example 10

Preparation of the Compound 1-10

Under nitrogen, the compound E (4 g, 9.7 mmol) that was prepared in Preparative Example 5, the compound R (3.1 g, 10.75 mmol), and Pd(PPh$_3$)$_4$ (0.3 g, 0.29 mmol) were put into the 2M K$_2$CO$_3$ aqueous solution (80 mL) and THF (120 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-10 (3.8 g, 83%).

MS [M+H]+=573

Example 11

Preparation of the Compound 1-139

Under nitrogen, the compound E (4 g, 9.7 mmol) that was prepared in Preparative Example 5, the compound L (4.2 g, 10.75 mmol), and Pd(PPh$_3$)$_4$ (0.3 g, 0.29 mmol) were put into the 2M K$_2$CO$_3$ aqueous solution (80 mL) and THF (120 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-139 (3.8 g, 83%).

MS [M+H]+=675

Example 12

Preparation of the Compound 1-140

Under nitrogen, the compound T (1.0 g, 3.0 mmol) that was prepared in Preparative Example 14, diphenylamine (2.09 g, 12.38 mmol), pd(dba)$_2$ (0.097 g, 0.17 mmol), P(t-Bu)$_3$ (0.05 g, 0.255 mmol) and sodium t-butoxide (2.45 g, 25.5 mmol) were put into toluene (100 mL), and refluxed for about 5 hours. After the reaction was finished, it was cooled to normal temperature, and the reaction mixture solution was put into the mixture solution of THF and H$_2$O. The organic layer was separated, dried with MgSO$_4$, and concentrated. It was purified with the column chromatography to obtain the compound 1-140 (0.82 g, 80%).

MS [M]=679

Example 13

Preparation of the Compound 1-40

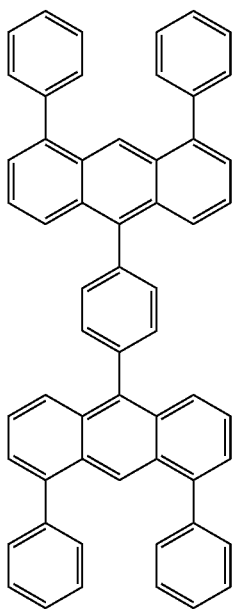

Molecular Weight = 734.95
Exact Mass = 734

Under nitrogen, the compound E (4 g, 9.7 mmol) that was prepared in Preparative Example 5, 1,4-benzene diboronic acid (0.95 g, 5.75 mmol), and Pd(PFh$_3$)$_4$ (0.3 g, 0.29 mmol) were put into the 2M K$_2$CO$_3$ aqueous solution (80 mL) and THF (120 mL), and refluxed and agitated for about 12 hours. After the reaction was finished, it was cooled to normal temperature, the organic layer was separated from the reaction mixture solution, and the solution was filtered to obtain the solid. The obtained solid was recrystallized with THF and ethanol to obtain the compound 1-40 (3.0 g, 78%).

MS [M+H]+=734

Experimental Example

A glass substrate (corning 7059 glass) on which a thin film of ITO (indium tin oxide) was coated to a thickness of 1,000 Å was immersed in distilled water having a dispersing agent dissolved therein to wash the substrate with ultrasonic waves. The dispersing agent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried, and then transported to a plasma washing machine. Using an oxygen plasma, the substrate was washed for 5 minutes and then transported to a vacuum depositing machine.

On the ITO electrode, 3,6-bis-2-naphthylphenylamino-N-[4-(2-naphthylphenyl)aminophenyl]carbazole (800 Å), 4,4'-bis[N-(1-naphthyl)-N-phenylamino]biphenyl (NPB) (300 Å), the host and the dopant described in the following Table 5 (Experimental Examples 1 to 14) (300 Å), and 9,10-bis-2-naphthyl-2-[4-(N-phenylbenzoimidazoyl)phenyl]anthracene (300 Å) were sequentially subjected to heat vacuum deposition to sequentially form the hole injection layer, the hole transport layer, the light emitting layer, and the electron transport layer. When the light emitting layer was formed, the amine compound that was represented by the following Formula D1 was doped as the dopant material (doping concentration 4%).

In Comparative Experimental Example, in the light emitting layer, the host material (H1) was used as the comparative compound, and the amine compound D1 was used as the dopant material (Experimental Example 15).

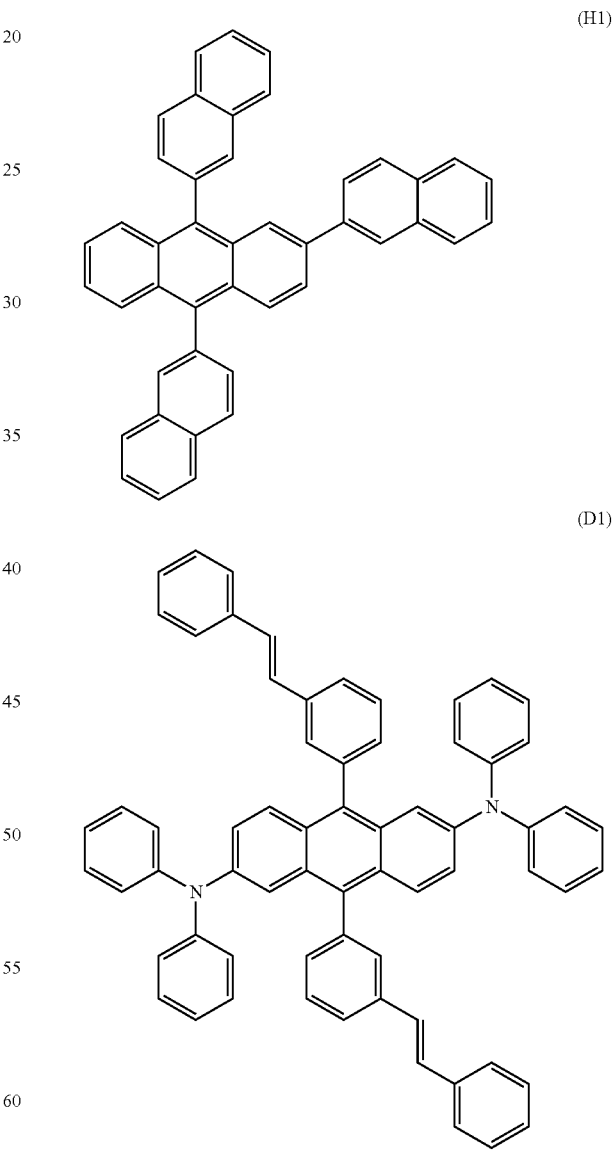

Lithium fluoride (LiF) and aluminum were sequentially deposited on the electron transport layer in thicknesses of 12 Å and 2,000 Å respectively, to form a cathode and prepare the organic light emitting device.

In the above process, the deposition rate of the organic material was maintained at 0.4 to 0.7 Å/sec and the deposition rate of lithium fluoride was maintained at 0.3 Å/sec and the deposition rate of aluminum was maintained at 2 Å/sec, respectively. The degree of vacuum upon deposition was maintained at $2 \times 10^{-7}$ to $5 \times 10^{-8}$ torr.

TABLE 5

| Experimental Example No. | Host material | Dopant material | Current efficiency (cd/A) | Life span (80%, hour) | Light emitting color |
|---|---|---|---|---|---|
| 1 | Example 1 | — | 7.8 | | Green |
| 2 | Example 2 | — | 8.0 | | Green |
| 3 | Example 3 | — | 7.5 | | Green |
| 4 | Example 4 | Example 10 | 6.7 | 150 | Blue |
| 5 | Example 4 | Example 1 | 23.2 | 360 | Green |
| 6 | Example 5 | Example 1 | 25.1 | 480 | Green |
| 7 | Example 6 | Example 1 | 23.5 | 320 | Green |
| 8 | Example 7 | — | 19.1 | | Green |
| 9 | Example 8 | — | 7.2 | | Blue green |
| 10 | Example 9 | — | 3.5 | | Blue |
| 11 | Example 10 | Example 1 | 24.5 | 400 | Green |
| 12 | Example 11 | — | 3.7 | | Blue |
| 13 | Example 12 | — | 7.4 | | yellow |
| 14 | Example 13 | Example 1 | 26.9 | 220 | Green |
| 15 | Comparative compound (H1) | D1 | 20.1 | 250 | Green |

The invention claimed is:

1. An anthracene derivative that is represented by the following Formula 1:

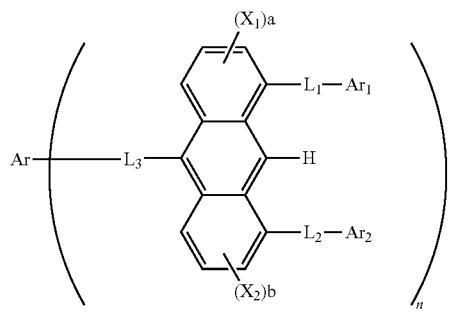

[Formula 1]

wherein n is an integer in the range of 1 to 3, in the case of when n is 2 or more, the structures in the parentheses are the same as or different from each other, $L_1$, $L_2$ and $L_3$ are the same as or different from each other, and are each independently a direct bond; or substituted or unsubstituted arylene, $Ar_1$ and $Ar_2$ are the same as or different from each other, and are each independently substituted or unsubstituted nonfused ring having 6 to 50 carbon atoms; substituted or unsubstituted fused ring aryl having 10 to 50 carbon atoms; substituted or unsubstituted nonfused ring or fused ring heteroaryl having 3 to 50 carbon atoms; substituted or unsubstituted fluorenyl; substituted or unsubstituted carbazolyl; or substituted or unsubstituted arylamine, Ar is substituted or unsubstituted nonfused ring having 6 to 50 carbon atoms; substituted or unsubstituted fused ring aryl having 10 to 50 carbon atoms; substituted or unsubstituted nonfused ring or fused ring heteroaryl having 3 to 50 carbon atoms; substituted or unsubstituted fluorenyl; substituted or unsubstituted carbazolyl; or substituted or unsubstituted arylamine, when n is 1, at least one of Ar, $Ar_1$, and $Ar_2$ is substituted or unsubstituted arylamine, a and b are 1;

$X_1$ and $X_2$ are hydrogen; and the arylamine is an amine group that is substituted by one or more aryl groups having 6 to 20 carbon atoms and the nitrogen atom of the amine group is not included in a fused or non-fused ring.

2. The anthracene derivative according to claim 1, wherein Formula 1 is represented by the following Formulas 2 to 5:

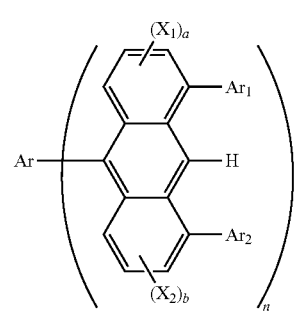

[Formula 2]

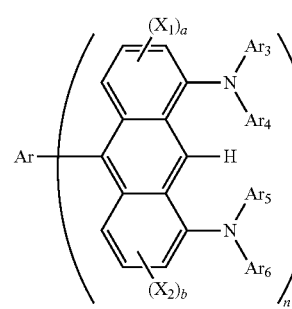

[Formula 3]

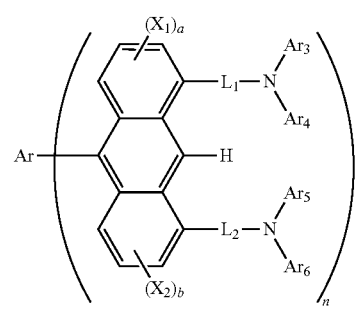

[Formula 4]

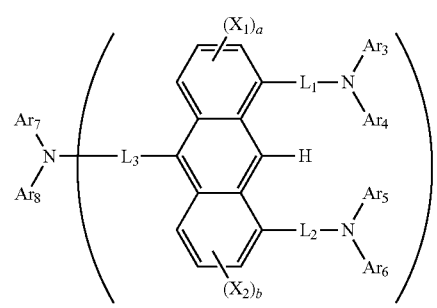

[Formula 5]

wherein Ar, $X_1$, $X_2$, $Ar_1$, $Ar_2$, $L_1$, $L_2$, $L_3$, a, b and n are the same as those defined by Formula 1, and $Ar_3$ to $Ar_8$ are substituted or unsubstituted nonfused ring having 6 to 50 carbon atoms; substituted or unsubstituted fused ring aryl having 10 to 50 carbon atoms; or substituted or unsubstituted nonfused ring or fused ring heteroaryl having 3 to 50 carbon atoms.

3. The anthracene derivative according to claim 1, wherein in Formula 1, n is 1, $Ar_1$ and $Ar_2$ are substituted or unsubstituted nonfused ring or fused ring aryl; substituted or unsubstituted fused ring heteroaryl; substituted or unsubstituted fluorenyl; or substituted or unsubstituted carbazolyl, and Ar is substituted or unsubstituted arylamine.

4. The anthracene derivative according to claim 1, wherein in Formula 1, n is 2, Ar is a group selected from the group consisting of the following structural formulas, and Ar is unsubstituted or substituted by one or more groups that are selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_3$~$C_{20}$ heterocycloalkyl group, a $C_6$~$C_{50}$ aryl group, a $C_5$~$C_{50}$ heteroaryl group, and an arylamine group:

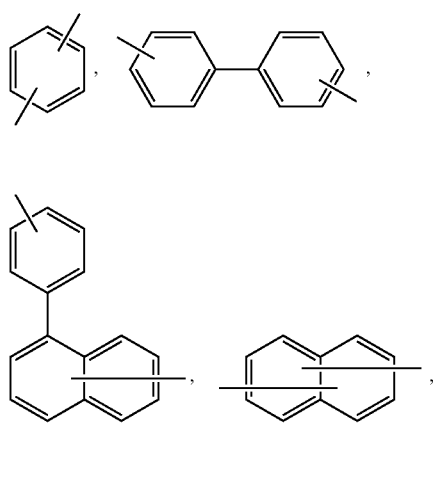

5. The anthracene derivative according to claim 1, wherein in Formula 1, n is 2, Ar is selected from the groups that are represented by the following structural formulas, and Ar is unsubstituted or substituted by one or more groups that are selected from the group consisting of a $C_1$~$C_{20}$ alkyl group, a $C_2$~$C_{20}$ alkenyl group, a $C_2$~$C_{20}$ alkynyl group, a $C_3$~$C_{20}$ cycloalkyl group, a $C_3$~$C_{20}$ heterocycloalkyl group, a $C_6$~$C_{20}$ aryl group and a $C_5$~$C_{20}$ heteroaryl group, and an arylamine group:

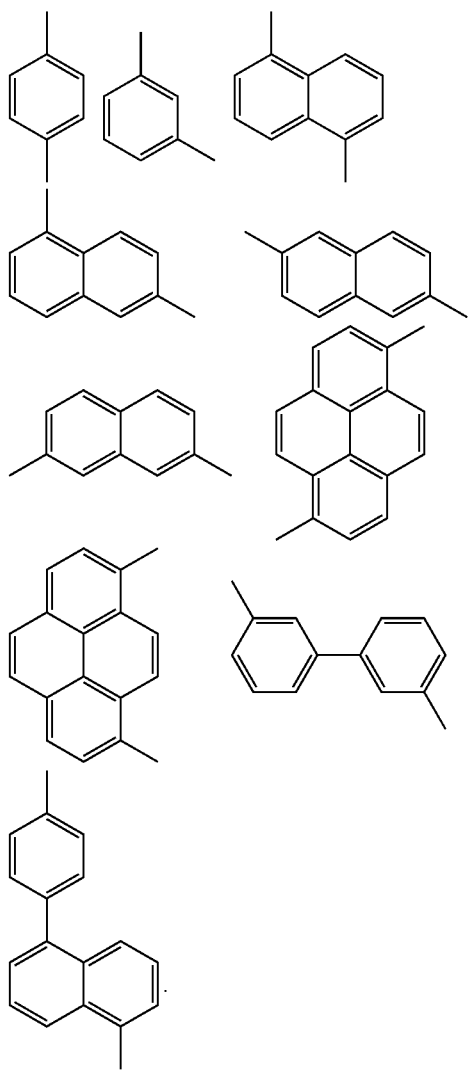

6. An anthracene derivative that is represented by the following Formula 1:

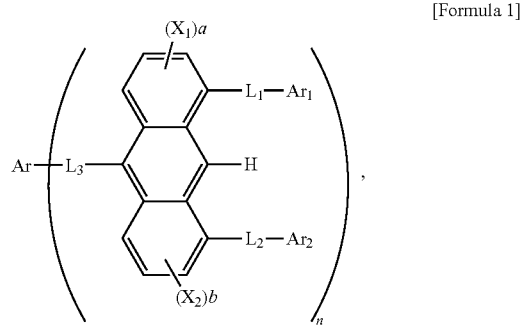

[Formula 1]

wherein in Formula 1, n is 1, a and b are 1, and Ar, $Ar_1$, $Ar_2$, $L_1$, $L_2$, $L_3$, $X_1$ and $X_2$ are substituent groups that are described in the following Table 1:

TABLE 1

| Formula | Ar | Ar₁ | Ar₂ | L₁ | L₂ | L₃ | X₁ | X₂ |
|---|---|---|---|---|---|---|---|---|
| 1-137 | diphenylamino-phenyl | phenyl | phenyl | direct bond | direct bond | direct bond | H | H |
| 1-138 | diphenylamino-phenyl | phenyl | phenyl | direct bond | direct bond | phenylene | H | H |
| 1-139 | diphenylamino-styryl-phenyl | phenyl | phenyl | direct bond | direct bond | phenylene | H | H |
| 1-140 | diphenylamino-phenyl | diphenylamino-phenyl | diphenylamino-phenyl | direct bond | direct bond | direct bond | H | H. |

7. The anthracene derivative according to claim 1, wherein in Formula 1, n is 2, and Ar, Ar₁, Ar₂, L₁, L₂, L₃, X₁ and X₂ are substituent groups that are described in the following Table 2:

TABLE 2

| Formula | Ar | Ar₁ | Ar₂ | L₁ | L₂ | L₃ | X₁ | X₂ |
|---|---|---|---|---|---|---|---|---|
| 1-40 | 1,4-phenylene | phenyl | phenyl | direct bond | direct bond | direct bond | H | H |
| 1-41 | 1,3-phenylene | phenyl | phenyl | direct bond | direct bond | direct bond | H | H |
| 1-42 | 1,5-naphthylene | phenyl | phenyl | direct bond | direct bond | direct bond | H | H |
| 1-43 | 2,7-naphthylene | phenyl | phenyl | direct bond | direct bond | direct bond | H | H |

TABLE 2-continued

| Formula | Ar | Ar₁ | Ar₂ | L₁ | L₂ | L₃ | X₁ | X₂ |
|---|---|---|---|---|---|---|---|---|
| 1-44 | 2,6-naphthalenediyl | phenyl | phenyl | direct bond | direct bond | direct bond | H | H |
| 1-45 | 2,7-naphthalenediyl | phenyl | phenyl | direct bond | direct bond | direct bond | H | H |
| 1-46 | pyrenediyl | phenyl | phenyl | direct bond | direct bond | direct bond | H | H |
| 1-47 | 9-phenylcarbazole-3,6-diyl | phenyl | phenyl | direct bond | direct bond | direct bond | H | H |
| 1-48 | 1,4-phenylene | pyridin-2-yl | pyridin-2-yl | direct bond | direct bond | direct bond | H | H |
| 1-49 | 1,3-phenylene | pyridin-2-yl | pyridin-2-yl | direct bond | direct bond | direct bond | H | H |
| 1-50 | 1,5-naphthalenediyl | pyridin-2-yl | pyridin-2-yl | direct bond | direct bond | direct bond | H | H |
| 1-51 | 1,7-naphthalenediyl | pyridin-2-yl | pyridin-2-yl | direct bond | direct bond | direct bond | H | H |
| 1-52 | 2,6-naphthalenediyl | pyridin-2-yl | pyridin-2-yl | direct bond | direct bond | direct bond | H | H |

TABLE 2-continued
| Formula | Ar | Ar₁ | Ar₂ | L₁ | L₂ | L₃ | X₁ | X₂ |
|---|---|---|---|---|---|---|---|---|
| 1-53 | 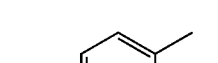 | 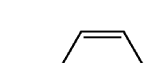 | 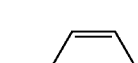 | direct bond | direct bond | direct bond | H | H |
| 1-54 | 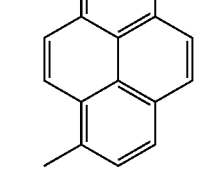 | 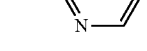 | 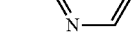 | direct bond | direct bond | direct bond | H | H |
| 1-55 | 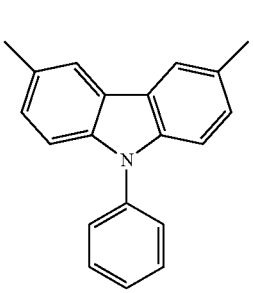 | 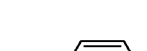 | 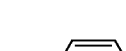 | direct bond | direct bond | direct bond | H | H |
| 1-56 | 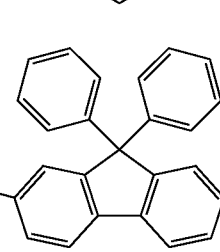 |  |  | direct bond | direct bond | direct bond | H | H |
| 1-57 | 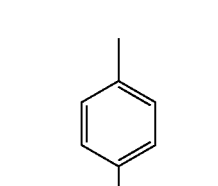 | 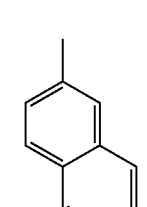 | 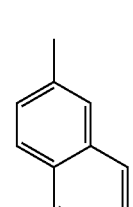 | direct bond | direct bond | direct bond | H | H |
| 1-58 | 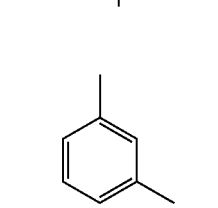 | 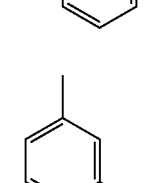 | 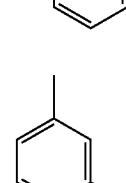 | direct bond | direct bond | direct bond | H | H |
| 1-59 | 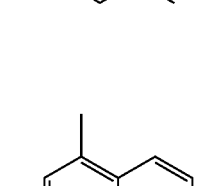 | 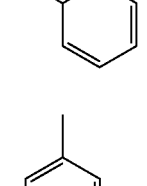 | 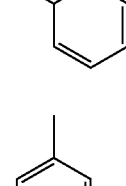 | direct bond | direct bond | direct bond | H | H |

TABLE 2-continued
| Formula | Ar | Ar₁ | Ar₂ | L₁ | L₂ | L₃ | X₁ | X₂ |
|---|---|---|---|---|---|---|---|---|
| 1-60 | 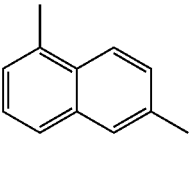 | 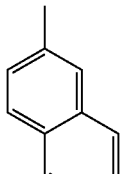 | 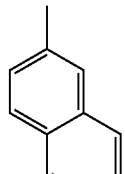 | direct bond | direct bond | direct bond | H | H |
| 1-61 | 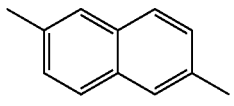 | 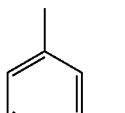 | 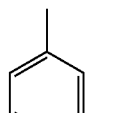 | direct bond | direct bond | direct bond | H | H |
| 1-62 | 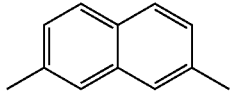 | 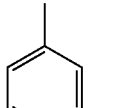 | 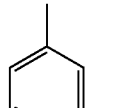 | direct bond | direct bond | direct bond | H | H |
| 1-63 | 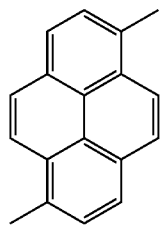 | 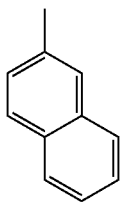 | 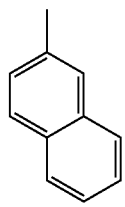 | direct bond | direct bond | direct bond | H | H |
| 1-64 | 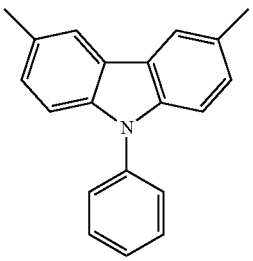 | 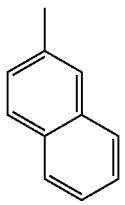 | 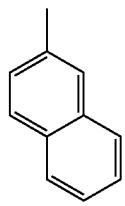 | direct bond | direct bond | direct bond | H | H |
| 1-65 | 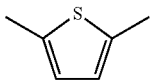 | 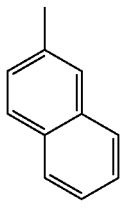 | 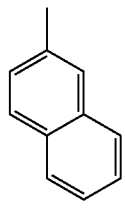 | direct bond | direct bond | direct bond | H | H |

TABLE 2-continued

| Formula | Ar | Ar₁ | Ar₂ | L₁ | L₂ | L₃ | X₁ | X₂ |
|---|---|---|---|---|---|---|---|---|
| 1-66 | 3-methyl-9-methylcarbazole | 4-biphenyl | 4-biphenyl | direct bond | direct bond | 1,4-phenylene | H | H. |

8. The anthracene derivative according to claim 1, wherein in Formula 1, n is 1, Ar₁ is —NAr₃Ar₄, Ar₂ is —NAr₅Ar₆, and Ar, Ar₃ to Ar₆, L₁, L₂, L₃, X₁ and X₂ are substituent groups that are described in the following Table 3:

TABLE 3

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-67 | 4-biphenyl | phenyl | phenyl | phenyl | phenyl | direct bond | direct bond | direct bond | H | H |
| 1-68 | 2-(4-phenyl)naphthyl | phenyl | phenyl | phenyl | phenyl | direct bond | direct bond | direct bond | H | H |
| 1-69 | 2-naphthyl | phenyl | phenyl | phenyl | phenyl | direct bond | direct bond | direct bond | H | H |
| 1-70 | 1-naphthyl | phenyl | phenyl | phenyl | phenyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-71 | | phenyl | phenyl | phenyl | phenyl | direct bond | direct bond | direct bond | H | H |
| 1-72 | | phenyl | phenyl | phenyl | phenyl | direct bond | direct bond | direct bond | H | H |
| 1-73 | | phenyl | phenyl | phenyl | phenyl | direct bond | direct bond | direct bond | H | H |
| 1-74 | | phenyl | phenyl | phenyl | phenyl | direct bond | direct bond | direct bond | H | H |
| 1-75 | | phenyl | phenyl | phenyl | phenyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-76 | (2-methyl-9,10-diphenylanthracenyl) | phenyl | phenyl | phenyl | phenyl | direct bond | direct bond | direct bond | H | H |
| 1-77 | (2-methyl-9,10-di(naphthalen-2-yl)anthracenyl) | phenyl | phenyl | phenyl | phenyl | direct bond | direct bond | direct bond | H | H |
| 1-78 | (4-(diphenylamino)tolyl) | phenyl | phenyl | phenyl | phenyl | direct bond | direct bond | direct bond | H | H |
| 1-79 | (N-phenyl-N-(4-styrylphenyl)-p-tolylamino) | phenyl | phenyl | phenyl | phenyl | direct bond | direct bond | direct bond | H | H |
| 1-80 | (tri-p-tolylamino) | phenyl | phenyl | phenyl | phenyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-81 | biphenyl | p-tolyl | p-tolyl | p-tolyl | p-tolyl | direct bond | direct bond | direct bond | H | H |
| 1-82 | 2-naphthyl-phenyl | p-tolyl | p-tolyl | p-tolyl | p-tolyl | direct bond | direct bond | direct bond | H | H |
| 1-83 | 2-naphthyl | p-tolyl | p-tolyl | p-tolyl | p-tolyl | direct bond | direct bond | direct bond | H | H |
| 1-84 | 1-naphthyl | p-tolyl | p-tolyl | p-tolyl | p-tolyl | direct bond | direct bond | direct bond | H | H |
| 1-85 | 2,2-diphenylvinyl-phenyl | p-tolyl | p-tolyl | p-tolyl | p-tolyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-86 | stilbene-tolyl | tolyl | tolyl | tolyl | tolyl | direct bond | direct bond | direct bond | H | H |
| 1-87 | 9,9-diphenylfluorenyl-tolyl | tolyl | tolyl | tolyl | tolyl | direct bond | direct bond | direct bond | H | H |
| 1-88 | 2,5-diaryl-thiophene | tolyl | tolyl | tolyl | tolyl | direct bond | direct bond | direct bond | H | H |
| 1-89 | triphenylpyrenyl | tolyl | tolyl | tolyl | tolyl | direct bond | direct bond | direct bond | H | H |
| 1-90 | 9,10-diphenylanthracenyl | tolyl | tolyl | tolyl | tolyl | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-91 | 9,10-bis(2-naphthyl)-2-methylanthracene | p-tolyl | p-tolyl | p-tolyl | p-tolyl | direct bond | direct bond | direct bond | H | H |
| 1-92 | 4-methyl-triphenylamine | p-tolyl | p-tolyl | p-tolyl | p-tolyl | direct bond | direct bond | direct bond | H | H |
| 1-93 | 4-methyl-N-phenyl-N-(4-styrylphenyl)aniline | p-tolyl | p-tolyl | p-tolyl | p-tolyl | direct bond | direct bond | direct bond | H | H |
| 1-94 | tri(p-tolyl)amine | p-tolyl | p-tolyl | p-tolyl | p-tolyl | direct bond | direct bond | direct bond | H | H |
| 1-95 | 2-naphthyl | biphenyl | biphenyl | biphenyl | biphenyl | direct bond | direct bond | direct bond | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-96 | 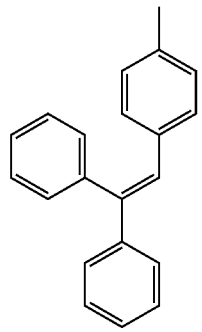 | 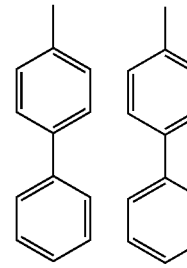 | 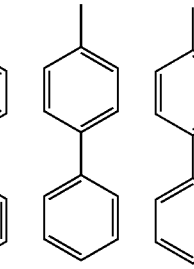 | 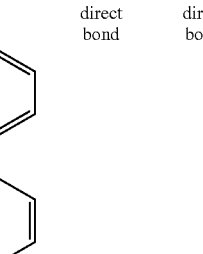 | 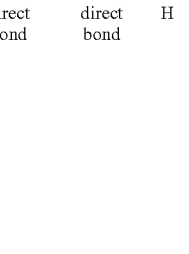 | direct bond | direct bond | direct bond | H | H |
| 1-97 | 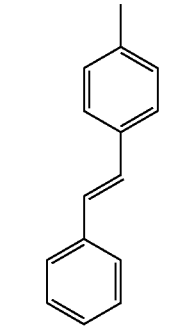 | 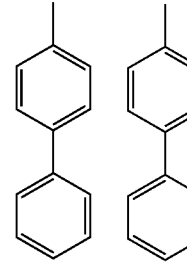 | 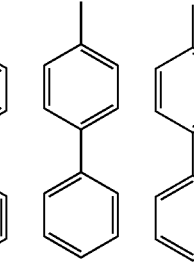 | 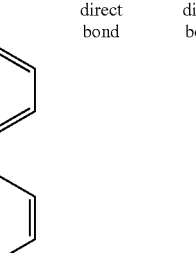 | 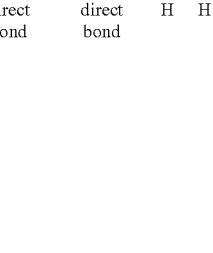 | direct bond | direct bond | direct bond | H | H |
| 1-98 | 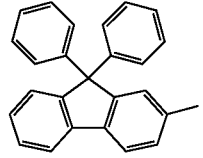 | 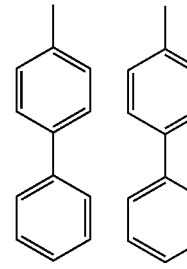 | 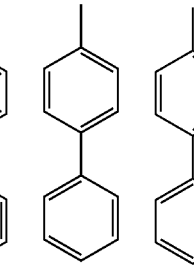 | 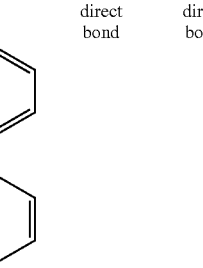 |  | direct bond | direct bond | direct bond | H | H |
| 1-99 | 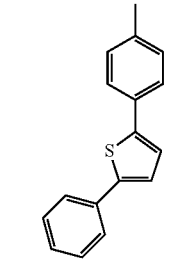 | 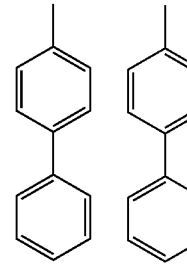 | 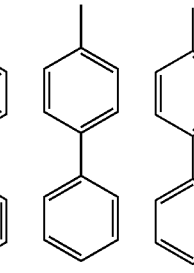 | 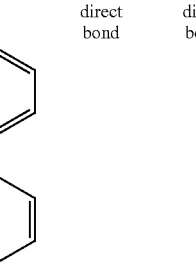 |  | direct bond | direct bond | direct bond | H | H |
| 1-100 | 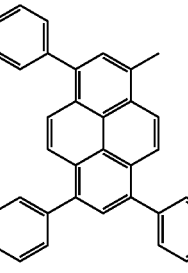 | 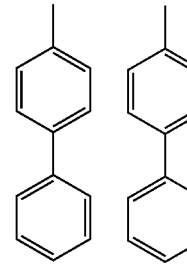 | 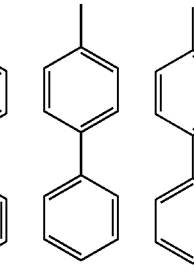 | 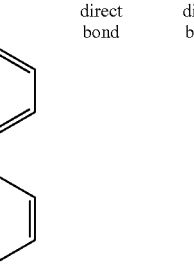 |  | direct bond | direct bond | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-101 | 2-methyl-9,10-diphenylanthracene | biphenyl | biphenyl | biphenyl | biphenyl | direct bond | direct bond | direct bond | H | H |
| 1-102 | 2-methyl-9,10-di(naphthalen-2-yl)anthracene | biphenyl | biphenyl | biphenyl | biphenyl | direct bond | direct bond | direct bond | H | H |
| 1-103 | triphenylamine | biphenyl | biphenyl | biphenyl | biphenyl | direct bond | direct bond | direct bond | H | H |
| 1-104 | N-phenyl-N-(4-styrylphenyl)aniline | biphenyl | biphenyl | biphenyl | biphenyl | direct bond | direct bond | direct bond | H | H |
| 1-105 | 4,4'-dimethyltriphenylamine | biphenyl | biphenyl | biphenyl | biphenyl | direct bond | direct bond | direct bond | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-106 | 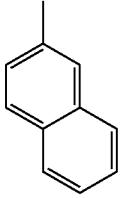 | 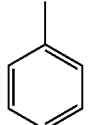 | 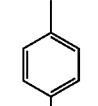 | 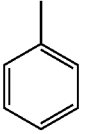 | 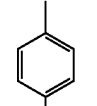 | direct bond | direct bond | direct bond | H | H |
| 1-107 | 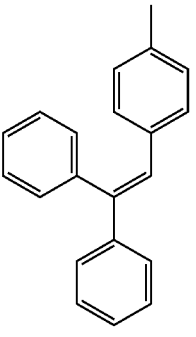 | 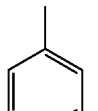 | 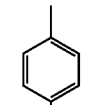 | 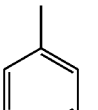 | 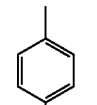 | direct bond | direct bond | direct bond | H | H |
| 1-108 | 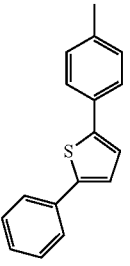 | 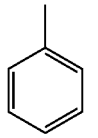 | 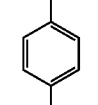 | 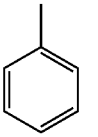 | 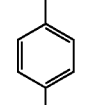 | direct bond | direct bond | direct bond | H | H |
| 1-109 | 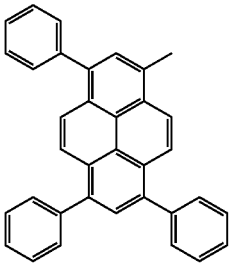 | 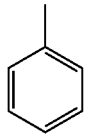 | 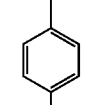 | 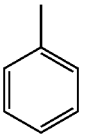 | 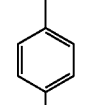 | direct bond | direct bond | direct bond | H | H |
| 1-110 | 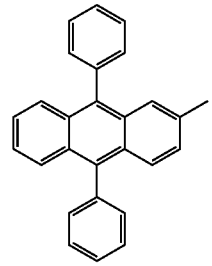 | 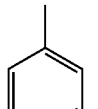 | 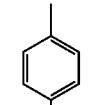 | 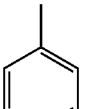 | 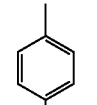 | direct bond | direct bond | direct bond | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-111 | 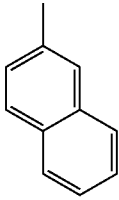 | 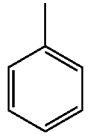 | 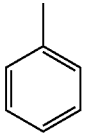 | 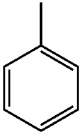 | 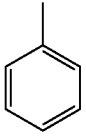 | 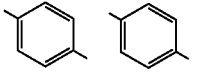 | 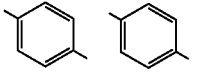 | direct bond | H | H |
| 1-112 | 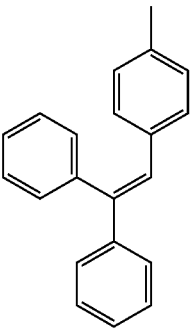 | 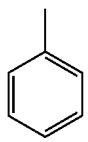 | 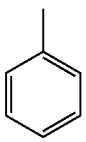 | 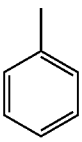 | 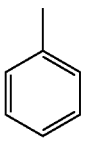 | 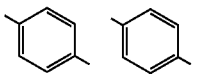 | 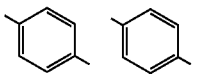 | direct bond | H | H |
| 1-113 | 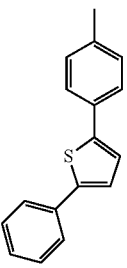 | 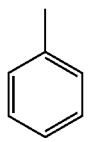 | 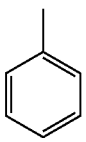 | 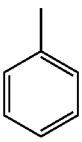 | 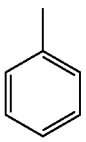 | 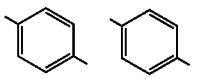 | 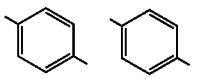 | direct bond | H | H |
| 1-114 | 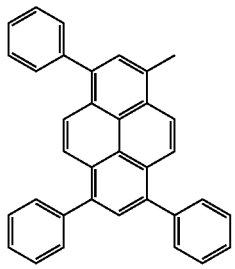 | 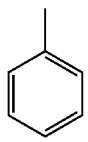 | 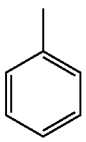 | 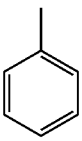 |  | 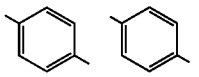 | 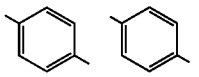 | direct bond | H | H |
| 1-115 | 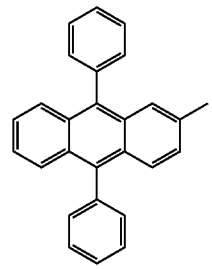 | 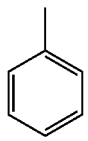 | 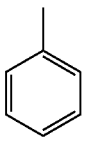 | 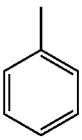 |  | 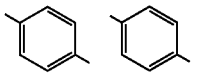 | 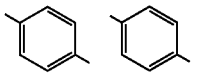 | direct bond | H | H |
| 1-116 | 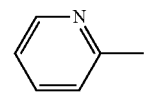 | 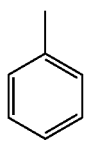 | 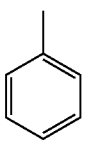 | 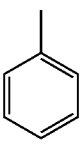 |  | 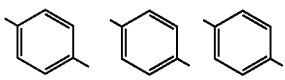 | 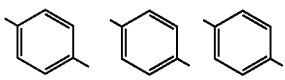 | | H | H |

TABLE 3-continued
| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-117 | 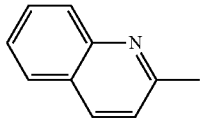 | 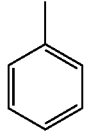 | 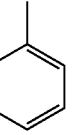 | 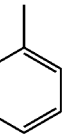 | 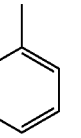 | 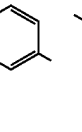 | 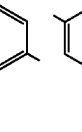 | 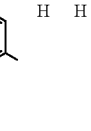 | H | H |
| 1-118 | 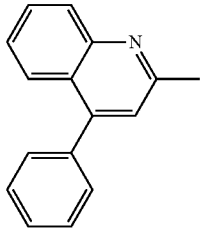 | 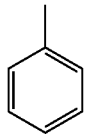 | 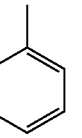 | 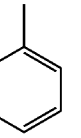 | 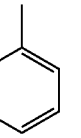 | 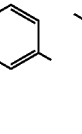 | 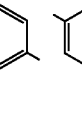 | 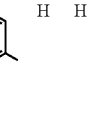 | H | H |
| 1-119 | 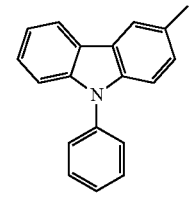 | 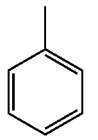 | 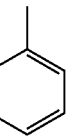 | 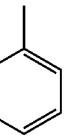 | 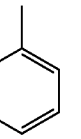 | 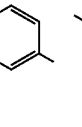 | 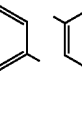 | 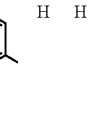 | H | H |
| 1-120 | 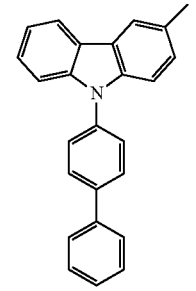 | 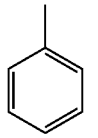 | 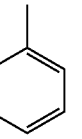 | 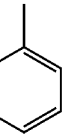 | 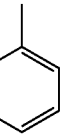 | 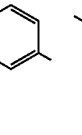 | 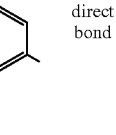 | direct bond | H | H |
| 1-121 |  | 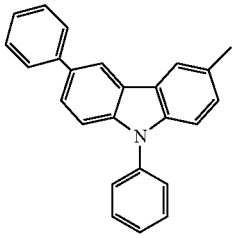 | 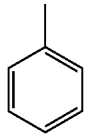 | 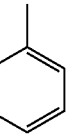 | 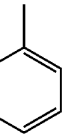 | 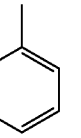 | 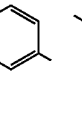 | direct bond | H | H |
| 1-122 | 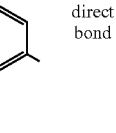 |  | 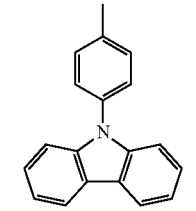 | 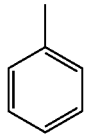 | 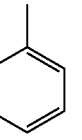 | 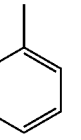 | 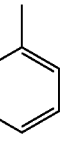 | 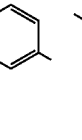 | H | H |
| 1-123 | 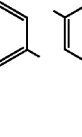 | 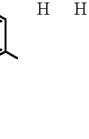 | 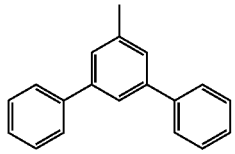 | 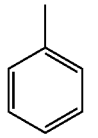 | 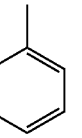 | 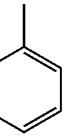 | 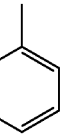 | direct bond | H | H |

TABLE 3-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-124 | 2-methylphenyl (H₃C-) | phenyl | phenyl | phenyl | phenyl | 1,4-phenylene | 1,4-phenylene | direct bond | H | H |
| 1-125 | 5-phenyl-2-thienyl | 3-methylphenyl | phenyl | 3-methylphenyl | phenyl | 1,4-phenylene | 1,4-phenylene | 1,4-phenylene | H | H |
| 1-141 | 9-phenyl-3-methylcarbazolyl | phenyl | phenyl | phenyl | phenyl | direct bond | direct bond | direct bond | H | H. |

9. The anthracene derivative according to claim 1, wherein in Formula 1, n is 2, Ar₁ is —NAr₃Ar₄, Ar₃ is —NAr₅Ar₆, and Ar, Ar₃ to Ar₆, L₁, L₂, L₃, X₁ and X₂ are substituent groups that are described in the following Table 4:

TABLE 4

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-126 | 1,4-dimethylphenyl | phenyl | phenyl | phenyl | phenyl | direct bond | direct bond | direct bond | H | H |
| 1-127 | 1,3-dimethylphenyl | phenyl | phenyl | phenyl | phenyl | direct bond | direct bond | direct bond | H | H |
| 1-128 | 1,5-dimethylnaphthyl | phenyl | phenyl | phenyl | phenyl | direct bond | direct bond | direct bond | H | H |
| 1-129 | 1,6-dimethylnaphthyl | phenyl | phenyl | phenyl | phenyl | direct bond | direct bond | direct bond | H | H |
| 1-130 | 2,6-dimethylnaphthyl | phenyl | phenyl | phenyl | phenyl | direct bond | direct bond | direct bond | H | H |

TABLE 4-continued

| Formula | Ar | Ar₃ | Ar₄ | Ar₅ | Ar₆ | L₁ | L₂ | L₃ | X₁ | X₂ |
|---|---|---|---|---|---|---|---|---|---|---|
| 1-131 | 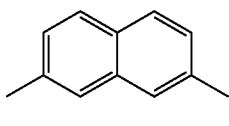 | 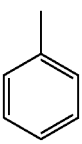 | 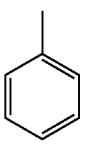 | 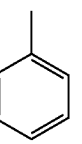 | 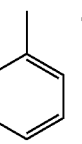 | direct bond | direct bond | direct bond | H | H |
| 1-132 | 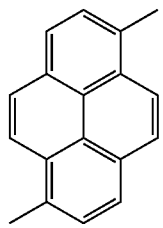 | 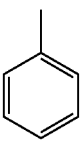 | 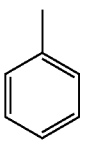 | 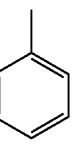 | 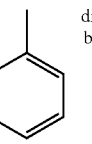 | direct bond | direct bond | direct bond | H | H |
| 1-133 | 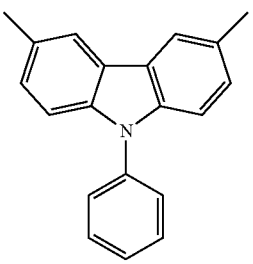 | 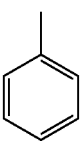 | 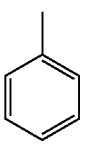 | 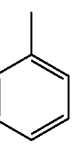 | 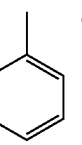 | direct bond | direct bond | direct bond | H | H |
| 1-134 | 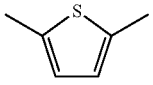 | 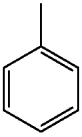 | 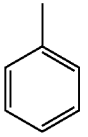 | 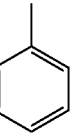 | 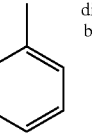 | direct bond | direct bond | direct bond | H | H |
| 1-135 | 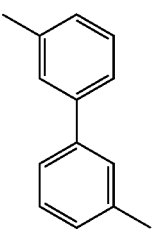 | 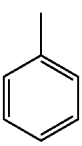 | 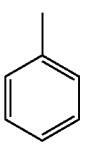 | 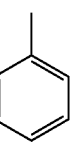 | 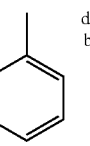 | direct bond | direct bond | direct bond | H | H |

10. An organic electronic device comprising:
a first electrode; a second electrode; and one or more organic material layers that are disposed between the first electrode and the second electrode, wherein one or more of the organic material layers comprise an anthracene derivative according to claim 1.

11. The organic electronic device according to claim 10, wherein the organic material layer comprises a hole injection layer and a hole transport layer, and the hole injection layer and the hole transport layer comprise an anthracene derivative.

12. The organic electronic device according to claim 10, wherein the organic material layer comprises a light emitting layer, and the light emitting layer comprises an anthracene derivative.

13. The organic electronic device according to claim 10, wherein the organic material layer comprises an electron transport layer, and the electron transport layer comprises an anthracene derivative.

14. The organic electronic device according to claim 10, wherein the organic electronic device is selected from the group consisting of an organic light emitting device, an organic solar cell, an organic photoconductor (OPC) and an organic transistor.

15. An organic electronic device comprising:
a first electrode; a second electrode; and one or more organic material layers that are disposed between the first electrode and the second electrode, wherein one or more of the organic material layers comprise an anthracene derivative according to claim 2.

16. An organic electronic device comprising:
a first electrode; a second electrode; and one or more organic material layers that are disposed between the first electrode and the second electrode, wherein one or more of the organic material layers comprise an anthracene derivative according to claim 6.

17. An organic electronic device comprising:
a first electrode; a second electrode; and one or more organic material layers that are disposed between the first electrode and the second electrode, wherein one or more of the organic material layers comprise an anthracene derivative according to claim 7.

18. An organic electronic device comprising:
a first electrode; a second electrode; and one or more organic material layers that are disposed between the first electrode and the second electrode, wherein one or more of the organic material layers comprise an anthracene derivative according to claim 8.

19. An organic electronic device comprising:
a first electrode; a second electrode; and one or more organic material layers that are disposed between the first electrode and the second electrode, wherein one or more of the organic material layers comprise an anthracene derivative according to claim 9.

* * * * *